(12) United States Patent
Furuichi et al.

(10) Patent No.: US 6,955,906 B2
(45) Date of Patent: Oct. 18, 2005

(54) BIOTIN BIOSYNTHETIC GENES HAVING BIOTIN SYNTHASE ACTIVITY

(75) Inventors: Yasuhiro Furuichi, Kamakura (JP); Tatsuo Hoshino, Kamakura (JP); Hitoshi Kimura, Odawara (JP); Tatsuya Kiyasu, Fujisawa (JP); Yoshie Nagahashi, Fujisawa (JP)

(73) Assignee: DSM Nutritional Products, Inc., Basel (CH)

( * ) Notice: Subject to any disclaimer, the term of this patent is extended or adjusted under 35 U.S.C. 154(b) by 0 days.

(21) Appl. No.: 10/763,933

(22) Filed: Jan. 23, 2004

(65) Prior Publication Data

US 2004/0137584 A1 Jul. 15, 2004

Related U.S. Application Data

(62) Division of application No. 10/033,078, filed on Dec. 27, 2001, now Pat. No. 6,723,544, which is a division of application No. 09/594,185, filed on Jun. 14, 2000, now Pat. No. 6,365,388, which is a division of application No. 08/935,263, filed on Sep. 22, 1997, now Pat. No. 6,117,669.

(30) Foreign Application Priority Data

Sep. 27, 1996 (EP) .............................. 96115540

(51) Int. Cl.$^7$ ............................ C12N 9/10; C12N 9/00; C12N 1/20; C12N 15/09; C07H 21/04
(52) U.S. Cl. .................... 435/193; 435/183; 435/252.3; 435/252.33; 435/320.1; 536/23.1; 536/23.2
(58) Field of Search ................................ 435/183, 193, 435/252.3, 252.33, 320.1; 536/23.1, 23.2

(56) References Cited

U.S. PATENT DOCUMENTS

| | | | |
|---|---|---|---|
| 5,096,823 A | 3/1992 | Gloeckler et al. | |
| 5,922,581 A | 7/1999 | Hoshino et al. | |
| 6,277,609 B1 | 8/2001 | Eddy | |
| 6,361,978 B1 | 3/2002 | Hoshino et al. | |

FOREIGN PATENT DOCUMENTS

| | | |
|---|---|---|
| EP | 0 375 525 | 6/1990 |
| EP | 0 635 572 | 1/1995 |
| EP | 0 747 483 | 12/1996 |
| EP | 0 799 895 | 10/1997 |
| WO | WO 87/01391 | 3/1987 |
| WO | WO 94/08023 | 4/1994 |

OTHER PUBLICATIONS

Broun et al. Science. Nov. 13, 1998;282(5392):1315–7.*
Ohsawa et al. Gene. Aug. 1, 1989;80(1):39–48.*
Ohsawa et al. Accession M27867. Aug. 2, 1994.*
Sanyal et al. Arch Biochem Biophys. Feb. 1, 1996;326(1):48–56.*
Cleary, et al., "Deletion and Complementation Analysis of the Biotin Gene Cluster of *Escherichia coli*," *J. Bacterial.*, 112:830–839 (1972).
Barker, et al., "Use of bio–Iac Fusion Strains to Study Regulation of Biotin Biosynthesis in *Escherichia coli*." *J. Bacterial.*, 143:789–800 (1980).
Tanaka, et al., "Site–Specific In vitro Binding of Plasmid pUB110 to *Bacillus subtilis* Membrane Factor," *J. Bacteriol.*, 154:1184–1194 (1983).
Otsuka, et al., "The *Escherichia coli* Biotin Biosynthetic Enzyme Sequences Predicted from the Nucleotide Sequence of the bio Operon," *J. Biol. Chem.*, 263:19577–19585 (1988).
Smith, "In vitro Mutagenesis," *Ann. Rev. Genet.*, 19:423–462 (1985).
Haima, et al., "The Effect of Restriction on Shotgun Cloning and Plasmid Stability in *Bacillus subtilis* Marburg," *Mol. Gen. Gent.*, 209:335–342 (1987).
Maniatis, et al., "Transformation of *Eschericha coli* by Plasmid DNA," *Molecular Cloning*, Cold Spring Harbor Laboratory Press, New York, pp. 252–253 (1982).
Derwent Abstract No. 86–216622 of Japanese Patent Kokai 149091/1986.
Derwent Abstract No. 87–23579 of Japanese Patent Kokai 155081/1987.
Derwent Abstract No. 90–226023 of Japanese Patent Kokai 180174/1991.
Derwent Abstract No. 90–072971 of Japanese Patent Kokai 27980/1990.
Derwent Abstract No. 91–358298 of Japanese Patent Kokai 240489/1991.
Derwent Abstract of EP 375 525.
Gloeckler et al. Accession A025679 (1994).
Ponting, C.P., "Issues in Predicting Protein Function from Sequence," *Brief, Bioinform*, 2(1):19–29 (2001).
Attwood, T.K., et al. "Which Craft is Best in Bioinformatics?" *Comput. Chem.*, 25(4):329–339 (2001).

* cited by examiner

*Primary Examiner*—Ponnathapu Achutamurthy
*Assistant Examiner*—Christian L. Fronda
(74) *Attorney, Agent, or Firm*—Bryan Cave LLP

(57) ABSTRACT

The present invention relates to the production process of biotin by fermentation using a genetically engineered microorganism, and DNA sequences and vectors to be used in such process.

8 Claims, 14 Drawing Sheets

B, BamHI; Bg, BglII; E, EcoRI; H, HindIII; Nc, NcoI; P, PstI; S, SalI

B, BamHI; Bg, BglII; E, EcoRI; H, HindIII; Nc, NcoI; P, PstI

```
5'CGCCAATGGCAGTTAACGCAGTAAATAGGGCAACATAAGAGATCGTTTTAGCTTTCAAGT  60
   GCGGTTACCGTCAATTGCGTCATTTATCCCGTTGTATTCTCTAGCAAAATCGAAAGTTCA
    A  G  I  A  T  L  A  T  F  L  A  V  Y  S  I  T  K  A  K  L
                                                      ◄--------ORF1

TTTCAACCTCCTTTTTTTAAAATTGGTAGGTAAAATGCCCACTATTAGTGTGCATGATTT  120
   AAAGTTGGAGGAAAAAAATTTTAACCATCCATTTTACGGGTGATAATCACACGTACTAAA
        RBS

Box1
   ATATTTTATATGTCAACCATTTATTATTTTAGTTAACATATAAAGCGCAATTAAAATGAC  180
   ----------------►      ◄----------------
   TATAAAATATACAGTTGGTAAATAATAAAATCAATTGTATATTTCGCGTTAATTTTACTG

-35                         -10
   AGACTTAGAAAAATATTGAAAATTAGTAATTGAACAATATTTTATTTGTGTGTTATTATA  240
   TCTGAATCTTTTTATAACTTTTAATCATTAACTTGTTATAAAATAAACACACAATAATAT
                                                              -10

Box2                            RBS
   CAATTTATATGTTAACTATTTTAAGATATAGTTAACATATAAAGGCTTGGAGGGAACAAA  300
   ----------------►         ◄----------------
   GTTAAATATACAATTGATAAAATTCTATATCAATTGTATATTTCCGAACCTCCCTTGTTT
                        -35

ORF2-------►
    M  T  G  E  M  L  I  Q  D  E  L  S  R  E  T  A  V  F  V  A
   TATGACAGGAGAAATGTTAATACAGGATGAACTTTCCAGAGAAACAGCGGTATTTGTGGC  360
   ATACTGTCCTCTTTACAATTATGTCCTACTTGAAAGGTCTCTTTGTCGCCATAAACACCG 5'
```

FIG. 10

```
ACTAACCCCTATGGTGTCCAGATTAAGCGTAATGTAGTATAGGATTTTAGTCAATTAGCA   60

-35                          -10
ATTTTTGAAATATTTAGTACGATCACATAATAGAATCATATATAATGATTAAAATATTAA  120

RBS
TTACAGAAAAGAGGTATTTTCATGCCATTCGTAAATCATGACAATGAAAGCCTTTACTAT  180
                     M  P  F  V  N  H  D  N  E  S  L  Y  Y
                     bioH --------▶

GAGGTTCACGGACAAGGTGATCCTTTATTGTTGATTATGGGGCTCGGCTATAACTCTTTA  240
 E  V  H  G  Q  G  D  P  L  L  L  I  M  G  L  G  Y  N  S  L
```

FIG. 11

```
TTATGATAAGTGTCTTTTTTTCGCCCCTTGATTTCTCCTAGATTAATGGATAATCAATTTA   60

-35                              -10    -------
TTATCATGTTCCTTTTCAAAGCTTGACAGTTTCATTGAGTCATGATTAGAATGTTTTATA  120

Box3
---------►        ◄---------------- RBS
TGTTAACCTATATTATTTTTAGTTAACATATAAAAAGGAGAATGGCTATGCACAGTGAAA  180
                                              M   H   S   E   K
                                              bioFII --------►

AACAATTACCTTGTTGGGAAGAAAAAATTAAGAAAGAACTGGCTTATTTAGAAGAGATAT  240
 Q   L   P   C   W   E   E   K   I   K   K   E   L   A   Y   L   E   E   I   S

CGCAAAAACGTGAACTCGTTTCAACGGAATTCGCCGAGCAGCCATGGCTTATGATCAACG  300
 Q   K   R   E   L   V   S   T   E   F   A   E   Q   P   W   L   M   I   N   G
```

FIG. 12

BIOTIN BIOSYNTHETIC GENES HAVING BIOTIN SYNTHASE ACTIVITY

This application is a divisional of U.S. application Ser. No. 10/033,078, filed Dec. 27, 2001, now U.S. Pat. No. 6,723,544, which is a divisional of U.S. application Ser. No. 09/594,185, filed Jun. 14, 2000, now U.S. Pat. No. 6,365,388, which is a divisional of U.S. application Ser. No. 08/935,263, filed Sep. 22, 1997, now U.S. Pat. No. 6,117,669.

BACKGROUND OF THE INVENTION

The present invention relates to the production process of biotin by fermentation using a genetically engineered organism.

Biotin is one of the essential vitamins for nutrition of animals, plants, and microorganisms, and very important as medicine or food additives.

Biotin biosynthesis of *Escherichia coli* has been studied well, and it has been clarified that biotin is synthesized from pimelyl CoA via 7 keto-8-amino pelargonic acid (KAPA), 7,8-diamino pelargonic acid (DAPA) and desthiobiotin (DTB) [*Escherichia coli* and *Salmonella typhimurium*, Cellular and Molecular Biology, 544, (1987)]. The analysis of genetic information involved in the biosynthesis of biotin has been advanced on *Escherichia coli* [J. Biol. Chem., 263, 19577, (1988)] and *Bacillus sphaericus* (U.S. Pat. No. 5,096,823). At least four enzymes are known to be involved in this biosynthetic pathway. These four enzymes are encoded by the bioA, bioB, bioD and bioF genes. The bioF gene codes for KAPA synthetase which catalyzes the conversion of pimelyl CoA to KAPA. The bioA gene codes for DAPA aminotransferase which converts KAPA to DAPA. The bioD gene codes for DTB synthetase which converts DAPA to DTB. The bioB gene codes for biotin synthase which converts DTB to biotin. It has been also reported that the bioC and bioH genes are involved in the synthesis of pimelyl CoA in *Escherichia coli*.

There are many studies on fermentative production of biotin. *Escherichia coli* (Japanese Patent Kokai No. 149091/1986 and Japanese Patent Kokai No. 155081/1987), *Bacillus sphaericus* (Japanese Patent Kokai No. 180174/1991), *Serratia marcescens* (Japanese Patent Kokai No. 27980/1990) and *Brevibacterium flavum* (Japanese Patent Kokai No. 240489/1991) have been used. But these processes have not yet been suitable for use in an industrial production process because of a low productivity. Moreover, large amounts of DTB, a biotin precursor, accumulates in the fermentation of these bacteria. Therefore, it has been assumed that the last step of the biotin biosynthetic pathway, from DTB to biotin, is a rate limiting step.

On the other hand, it was found that a bacterial strain belonging to the genus *Kurthia* produces DTB and small amounts of biotin. Also mutants which produce much larger amounts of biotin were derived from wild type strains of the genus *Kurthia* by selection for resistance to biotin antimetabolites acidomycin (ACM), 5-(2-thienyl)-valeric acid (TVA) and alpha-methyl desthiobiotin (MeDTB). However, in view of the still low biotin titers it is desirable to apply genetic engineering to improve the biotin productivity of such mutants.

SUMMARY OF THE INVENTION

The present invention relates therefore to the chromosomal DNA fragments carrying the genes involved in the biotin biosynthesis of *Kurthia* sp. The isolated chromosomal DNA fragments carry 8 genes, the bioA, bioB, bioC, bioD, bioF, bioFII, bioH and bioHII genes, and transcriptional regulatory sequences. The bioFII gene codes for an isozyme of the bioF gene product. The bioHII gene codes for an isozyme of the bioH gene product.

The present invention further relates to *Kurthia* sp. strains in which at least one gene involved in biotin biosynthesis is amplified, and also to the production process of biotin by this genetically engineered *Kurthia* sp. strain.

Although the DNA fragment mentioned above may be of various origins, it is preferable to use the strains belonging to the genus *Kurthia*. Specific examples of such strains include, for example, *Kurthia* sp. 538-6 (DSM No. 9454) and its mutant strains by selection for resistance to biotin antimetabolites such as *Kurthia* sp. 538-KA26 (DSM No. 10609).

BRIEF DESCRIPTION OF THE FIGURES

Before the present invention is explained in more detail by referring to the following examples a short description of the enclosed Figures is given:

FIG. 10: Nucleotide sequence between the ORF1 and ORF2 genes of *Kurthia* sp. 538-KA26.

FIG. 11: Nucleotide sequence of the promoter region of the bioH gene cluster.

FIG. 12: Nucleotide sequence of the promoter region of the bioFII gene cluster.

DETAILED DESCRIPTION OF THE INVENTION

Figure 1:
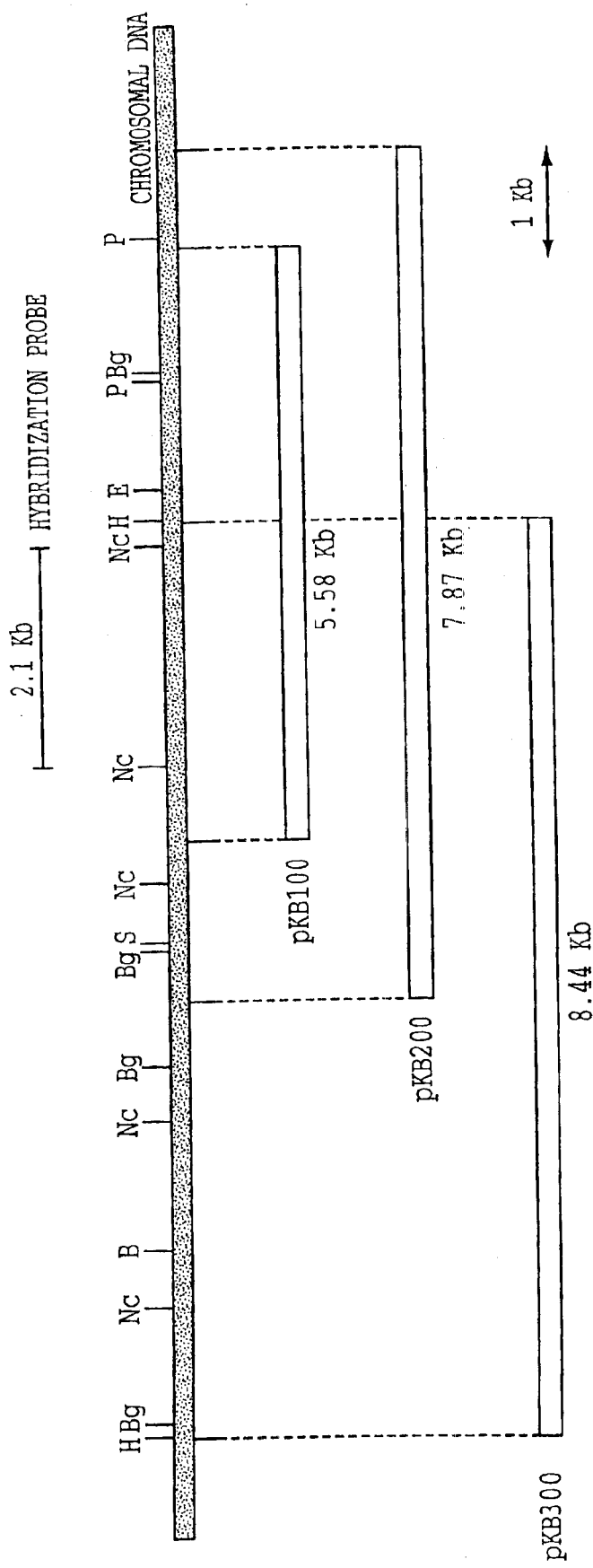
FIG. 1: Restriction maps of pKB100, pKB200 and pKB300.

Generally speaking the present invention is directed to DNA molecules comprising polynucleotides encoding polypeptides represented by SEQ ID Nos. 2, 4, 6, 8, 10, 12, 14 or 16, and functional derivatives of these polypeptides which contain addition, insertion, deletion and/or substitution of one or more amino acid residue(s), and to DNA molecules comprising polynucleotides which hybridize under stringent hybridizing conditions to polynucleotides which encode such polypeptides and functional derivatives. The invention is also directed to vectors comprising one or more such DNA sequences, for example, a vector wherein said DNA sequences are functionally linked to promoter sequence(s). The invention is further directed to biotin-expressing cells, said cells having been transformed by one or more DNA sequences or vector(s) as defined above, and a process for the production of biotin which comprises cultivating a biotin-expressing cell as defined above in a culture medium to express biotin into the culture medium, and isolating the resulting biotin from the culture medium by methods known in the art. Any conventional culture medium and culturing conditions may be used in accordance with the invention. Preferably, such a process is carried out wherein the cultivation is effected from 1 to 10 days, preferably from 2 to 7 days, at a pH from 5 to 9, preferably from 6 to 8, and a temperature range from 10 to 45° C., preferably from 25 to 30° C.

Finally, the present invention is also directed to a process for the preparation of pharmaceutical, food or feed compositions characterized therein that biotin obtained by such processes is mixed with one or more generally used additives with which a man skilled in the art is familiar.

The DNA molecules of the invention may be produced by any conventional means, such as by the techniques of genetic engineering and automated gene synthesis known in the art.

A detailed method for isolation of DNA fragments carrying the genes coding for the enzymes involved in the biotin biosynthesis from these bacterial strains is described below.

Therefore, DNA can be extracted from *Kurthia* sp. 538-KA26 by the known phenol method. Such DNA is then partially digested by Sau3AI and ligated with pBR322 digested by BamHI to construct a genomic library of *Kurthia* sp. 538-KA26.

Biotin auxotrophic mutants which lack the biosynthetic ability to produce biotin are transformed with the genomic library obtained above, and transformants showing biotin prototrophy are selected. The selected transformants have the genomic DNA fragments complementing deficient genes in the biotin auxotrophic mutants. As biotin auxotrophic mutants, *Escherichia coli* R875 (bioB⁻), R877 (bioD⁻), BM7086 (bioH⁻) and R878 (bioC⁻) (J. Bacteriol., 112, 830–839, (1972) and J. Bacteriol., 143, 789–800, (1980) can be used. The transformation of such *Escherichia coli* strains can be carried out according to a conventional method such as the competent cell method [*Molecular Cloning*, Cold Spring Harbor Laboratory Press, 252, (1982)].

In the present invention, a hybrid plasmid which complements the bioB deficient mutant of *Escherichia coli* was obtained in the manner described above. The obtained hybrid plasmid is named pKB100. The pKB100 corresponds to plasmid pBR322 carrying a 5.58 Kb of a genomic DNA fragment from *Kurthia* sp. 538-KA26, and its restriction cleavage map is shown in FIGS. 1 and 2.

Figure 3:
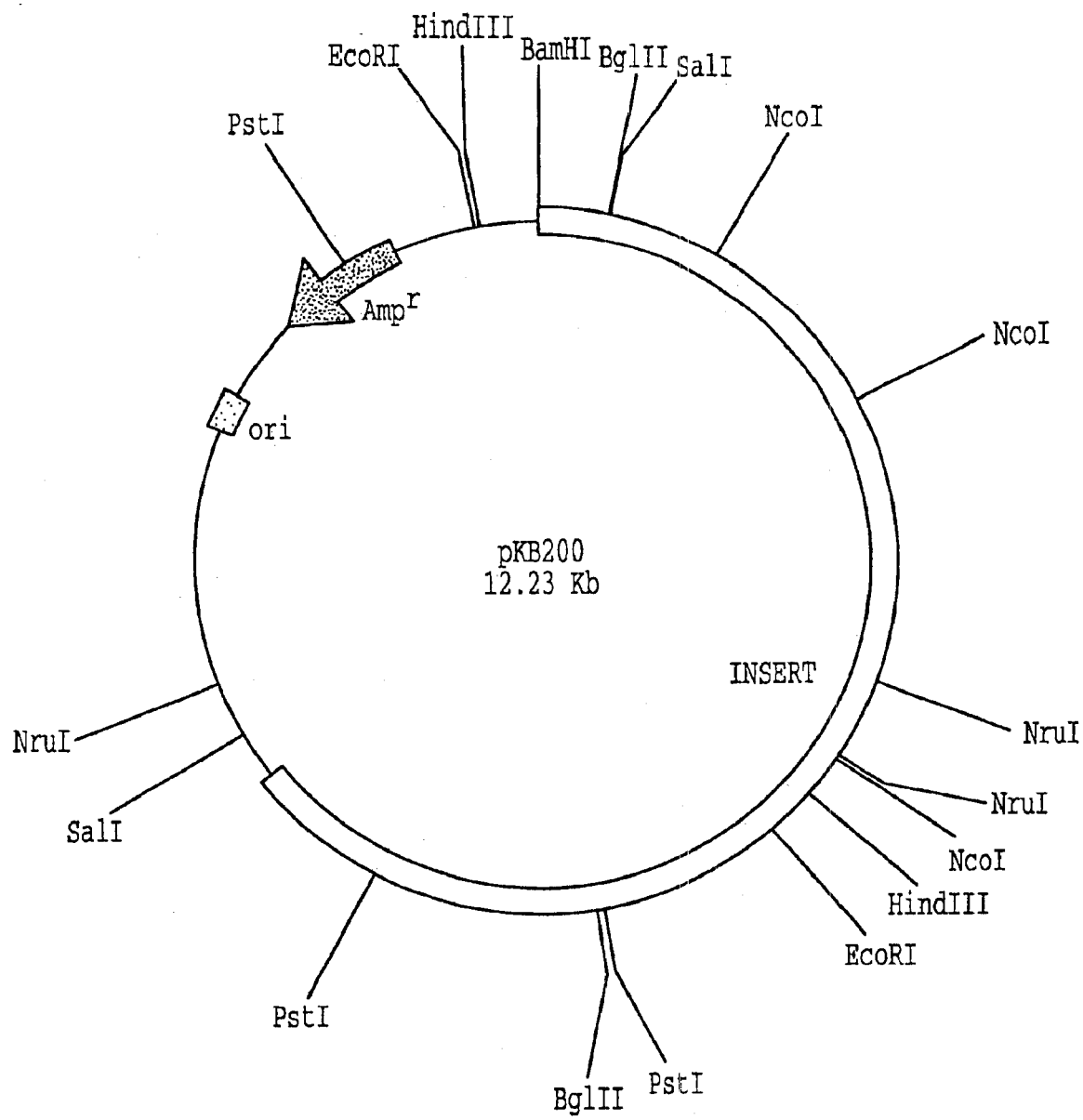
FIG. 3: Structure of pKB200.
Figure 9A:
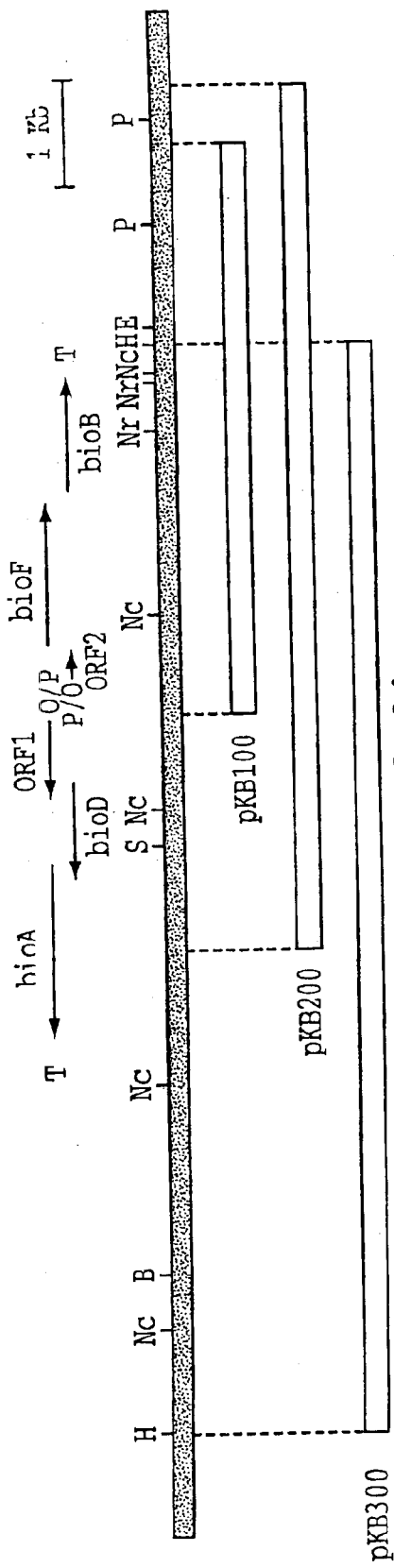
FIG. 9: Gene organizations of the gene clusters involved in biotin biosynthesis of *Kurthia* sp. 538-KA26.
Figure 9B:
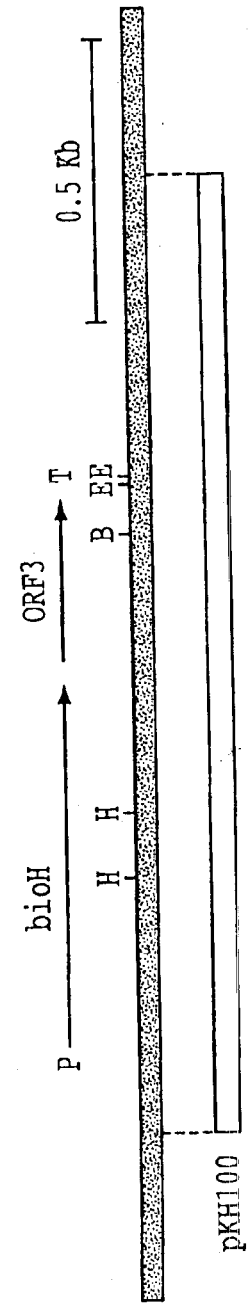
Figure 9C:
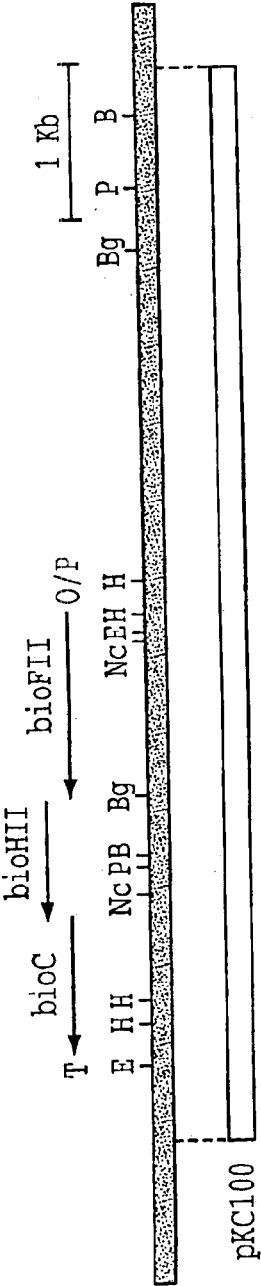

The hybrid plasmid named pKB200 which complements the bioD deficient mutant of *Escherichia coli* was also obtained as described above. The pKB200 corresponds to plasmid pBR322 carrying a 7.87 Kb of genomic DNA fragment from *Kurthia* sp. 538-KA26, and its restriction cleavage map is shown in FIGS. 1 and 3. The genomic DNA fragment in pKB200 completely overlapps with the inserted fragment of the pKB100 and carries the bioF, bioB, bioD, ORF1 and ORF2 genes and a part of the bioA gene of *Kurthia* sp. 538-KA26 as shown in FIG. 9-A.

The complete bioA gene of *Kurthia* sp. 538-KA26 can be isolated by conventional methods, such as colony hybridization using a part of the genomic DNA fragment in pKB200 as a probe. The whole DNA of *Kurthia* sp. 538-KA26 is digested with a restriction enzyme such as HindIII and ligated with a plasmid vector cleaved by the same restriction enzyme. Then, *Escherichia coli* is transformed with the hybrid plasmids carrying genomic DNA fragments of *Kurthia* sp. 538-KA26 to construct a genomic library. As a vector and *Escherichia coli* strain, the pUC19 [Takara Shuzo Co.(Higashiiru, Higashinotohin, Shijodohri, Shirnogyo-ku, Kyoto-shi, Japan)] and *Escherichia coli* JM109 (Takara Shuzo Co.) can be used, respectively.

Figure 2:
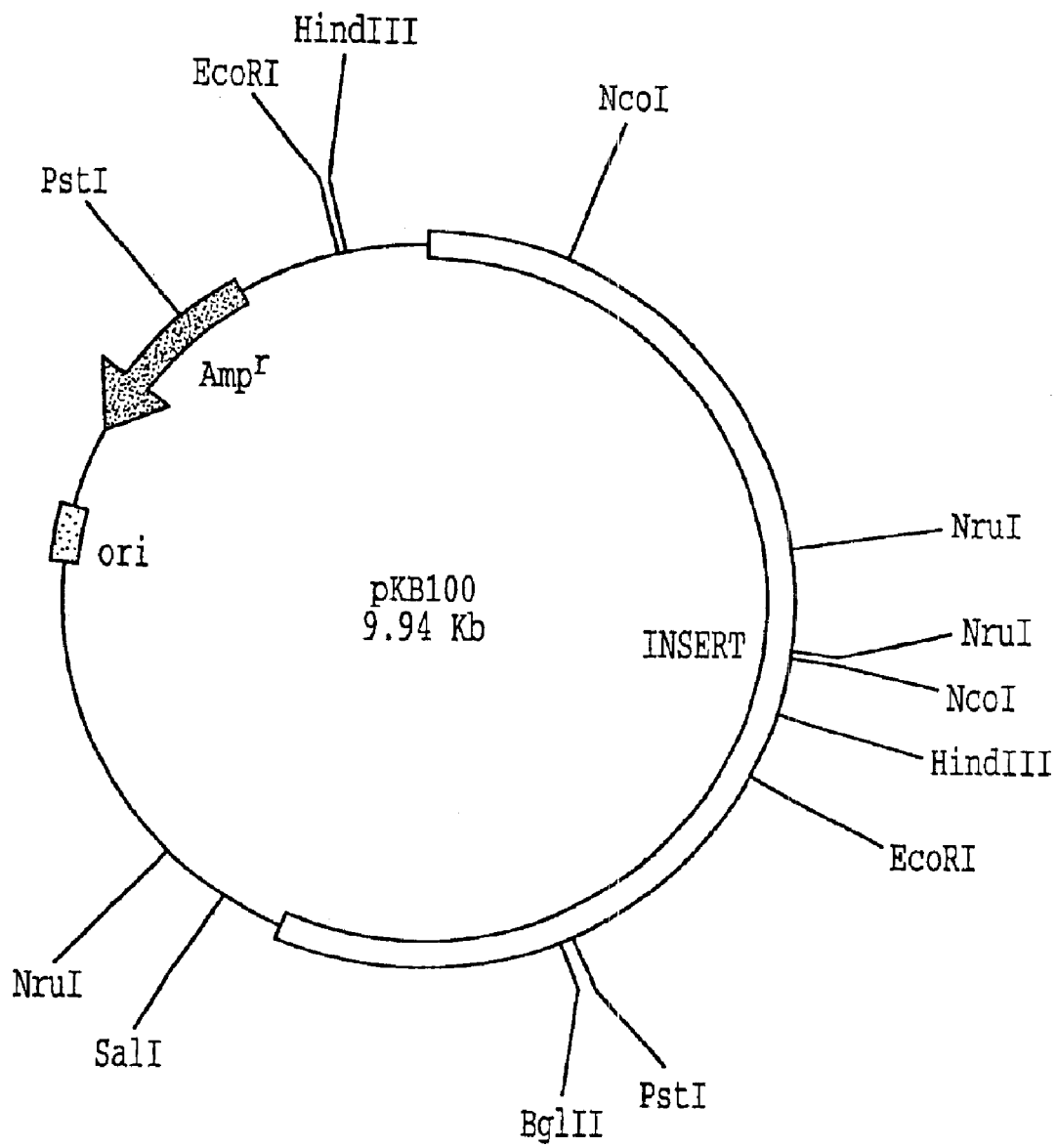
FIG. 2: Structure of pKB100.

The hybrid plasmid named pKB300 carrying a 8.44 Kb genomic DNA fragment from *Kurthia* sp. 538-KA26 was obtained by colony hybridization and its restriction cleavage map is shown in FIG. 1. The genomic DNA fragment in the pKB300 carries two gene clusters involved in the biotin biosynthesis of *Kurthia* sp. 538-KA26 as shown in FIG. 9-A. One cluster consists of the ORF1, bioD and bioA genes. Another cluster consists of the ORF2, bioF and bioB genes. The nucleotide sequences of the bioD and bioA genes are shown in SEQ ID No. 1 and SEQ ID NO: 3, respectively. The predicted amino acid sequences of the bioD and bioA gene products are shown in SEQ ID NO: 2 and SEQ ID NO: 4, respectively. The bioD gene codes for a polypeptide of 236 amino acid residues with a molecular weight of 26,642. The bioA gene codes for a polypeptide of 460 amino acid residues with a molecular weight of 51,731. The ORF1 gene codes for a polypeptide of 194 amino acid residues with a molecular weight of 21,516, but the biological function of this gene product is unknown.

The nucleotide sequences of the bioF and bioB genes are shown in SEQ ID NO: 5 and SEQ ID NO: 7, respectively. The predicted amino acid sequences of the bioF and bioB gene products are SEQ ID NO: 6 and SEQ ID NO: 8, respectively. The bioF gene codes for a polypeptide of 387 amino acid residues with a molecular weight of 42,619. The bioB gene codes for a polypeptide of 338 amino acid residues with a molecular weight of 37,438. The ORF2 gene codes for a polypeptide of 63 amino acid residues with a molecular weight of 7,447, but the biological function of this gene product is unknown. Inverted repeat sequences which are transcriptional terminator signals are found downstream of the bioA and bioB genes. As shown in FIG. 10, two transcriptional promoter sequences which initiate transcriptions in both directions are found between the ORF1 and ORF2 genes. Furthermore, there are two inverted repeat sequences named Box1 and Box2 involved in the negative control of the transcriptions between each promoter sequence and each translational start codon.

In addition, two hybrid plasmids which complement the biotin auxotrophic mutants of *Escherichia coli* were obtained in the manner described above. The hybrid plasmid named pKH100 complements the bioH deficient mutant, and the hybrid plasmid named pKC100 the bioC mutant. pKH100 (FIGS. 4 and 5) has a 1.91 Kb genomic DNA fragment from *Kurthia* sp. 538-KA26 carrying a gene cluster consisting of the bioH and ORF3 genes as shown in FIG. 9-B. The nucleotide sequence of the bioH gene and the predicted amino acid sequence of this gene product are shown in SEQ ID NO: 9 and SEQ ID NO: 10, respectively. The bioH gene codes for a polypeptide of 267 amino acid residues with a molecular weight of 29,423. The ORF3 gene codes for a polypeptide of 86 amino acid residues with a molecular weight of 9,955, but the biological function of this gene product is unknown. A promoter sequence is found upstream of the bioH gene as shown in FIG. 11, and there is an inverted repeat sequence which is the transcriptional terminator downstream of the ORF3 genes. Since the promoter region has no inverted sequence such as Box1 and Box2, it is expected that the expressions of these genes are not regulated.

Figure 6:
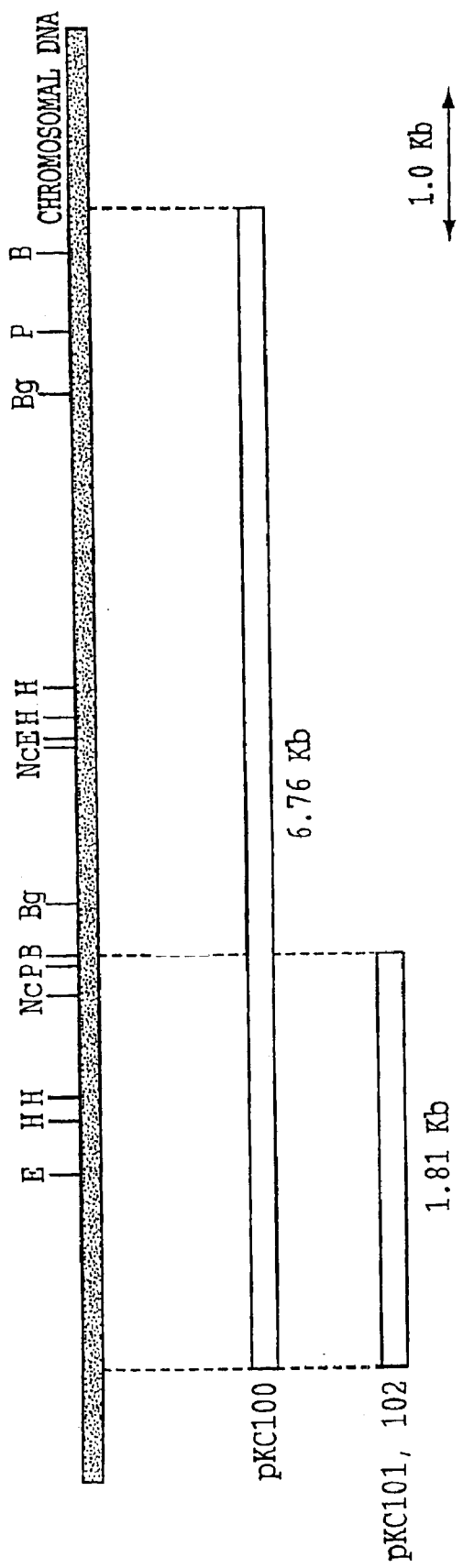
FIG. 6: Restriction maps of pKC100, pKC101 and pKC102.
Figure 7:
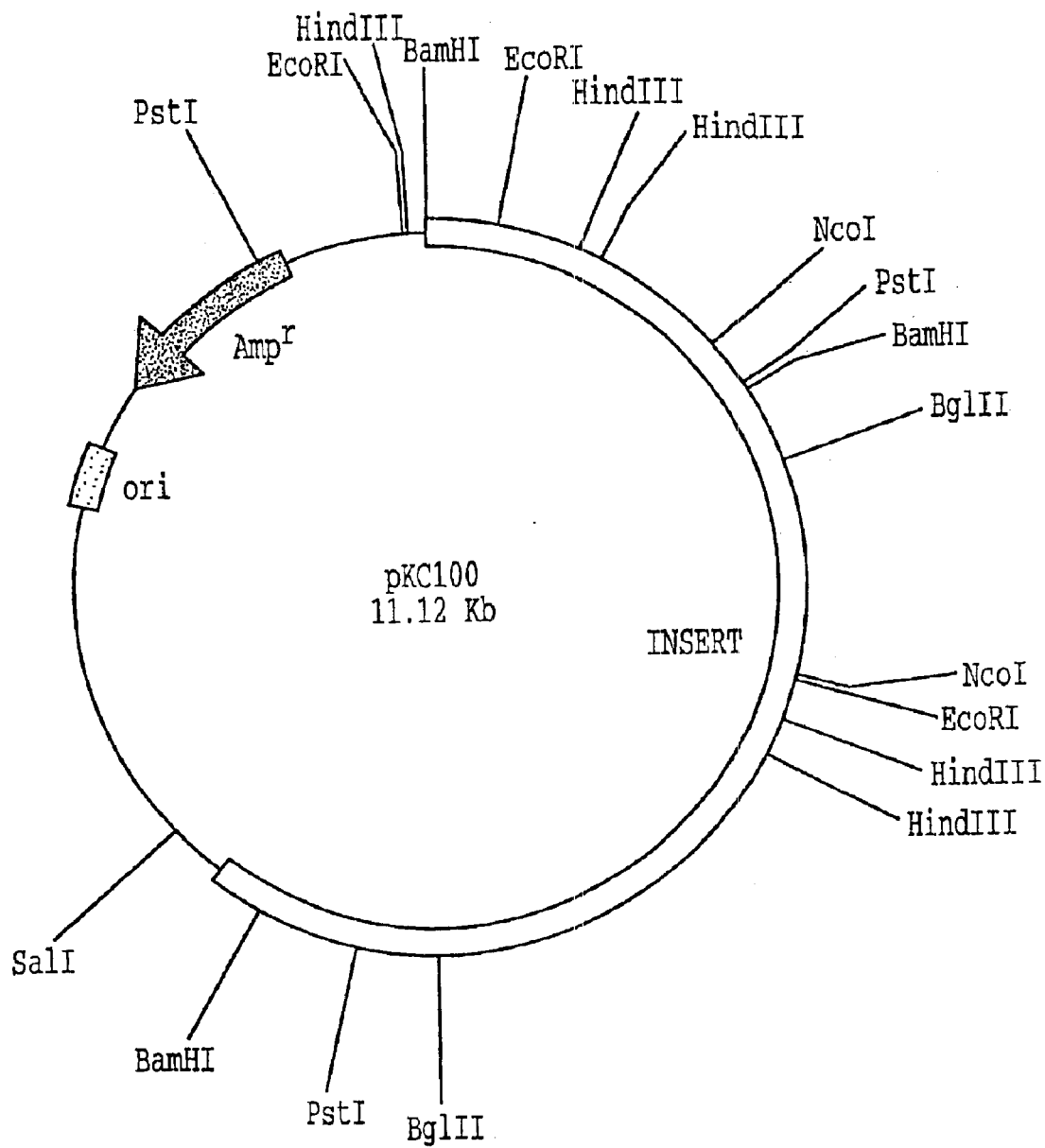
FIG. 7: Structure of pKC100.

On the other hand, pKC100 carries a 6.76 Kb genomic DNA fragment from *Kurthia* sp. 538-KA26 as shown in FIGS. 6 and 7. The genomic DNA fragment in pKC100 carries a gene cluster consisting of the bioFII, bioHII and bioC genes as shown in FIG. 9-C. The bioHII and bioFII genes are genes for isozymes of the bioH and bioF genes, respectively, because the bioHII and bioFII genes complement the bioH deficient and the bioF deficient mutants of *Escherichia coli,* respectively. The nucleotide sequences of the bioFII, bioHII and bioC genes are shown in SEQ ID NO: 11, SEQ ID NO: 13 and SEQ ID NO: 15, respectively. The predicted amino acid sequences of the bioFII, bioHII and bioC gene products are shown in SEQ ID NO: 12, SEQ ID NO: 14 and SEQ ID NO: 16, respectively. The bioFII gene codes for a polypeptide of 398 amino acid residues with a molecular weight of 44,776. The bioHII gene codes for a polypeptide of 248 amino acid residues with a molecular weight of 28,629. The bioC gene codes for a polypeptide of 276 amino acid residues with a molecular weight of 31,599. A promoter sequence is found upstream of the bioFII gene, and there is an inverted repeat sequence named Box3 in the promoter region as shown in FIG. 12. The transcription of these genes terminates at an inverted repeat sequence existing downstream of the bioC gene. Since the nucleotide sequence of Box3 is significantly similar to those of Box1 and Box2. expressions of these genes is estimated to be regulated similarly to the bioA and bioB gene clusters.

Needless to say, the nucleotide sequences and amino acid sequences of the genes isolated above are artificially changed in some cases, e.g., the initiation codon GTG or TTG may be converted into an ATG codon.

Therefore the present invention is also directed to functional derivatives of the polypeptides of the present case. Such functional derivatives are defined on the basis of the amino acid sequence of the present invention by addition, insertion, deletion and/or substitution of one or more amino acid residues of such sequences wherein such derivatives still have the same type of enzymatic activity as the corresponding polypeptides of the present invention. Such activities can be measured by any assays known in the art or specifically described herein. Such functional derivatives can be made either by chemical peptide synthesis known in the art or by recombinant means on the basis of the DNA sequences as disclosed herein by methods known in the state of the art, such as, e.g., that disclosed by Sambrook et al. (*Molecular Cloning,* Cold Spring Harbour Laboratory Press, New York, USA, second edition 1989). Amino acid exchanges in proteins and peptides which do not generally alter the activity of such molecules are known in the state of the art and are described, for example, by H. Neurath and R. L. Hill in "The Proteins" (Academix Press, New York, 1979, see especially FIG. 6, page 14). The most commonly occurring exchanges are: Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, Asp/Gly as well as the reverse.

Furthermore the present invention is not only directed to the DNA sequences as disclosed e.g., in the sequence listing as well as their complementary strands, but also to those which include these sequences, DNA sequences which hybridize under Standard Conditions with such sequences or fragments thereof and DNA sequences, which because of the degeneration of the genetic code, do not hybridize under Standard Conditions with such sequences but which code for polypeptides having exactly the same amino acid sequence.

"Standard Conditions" for hybridization mean in this context the conditions which are generally used by a man skilled in the art to detect specific hybridization signals and which are described, e.g., by Sambrook et al., (s.a.) or preferably so-called stringent hybridization and non-stringent washing conditions, or more preferably so-called stringent hybridization and stringent washing conditions a man skilled in the art is familiar with and which are described, e.g., in Sambrook et al. (s.a.). For purposes of the present invention, stringent hybridization conditions are carried out by hybridizing and washing in 0.2×SSC at about 65° C.

DNA sequences which are derived from the DNA sequences of the present invention either because they hybridize with such DNA sequences (see above) or can be constructed by the polymerase chain reaction by using primers designed on the basis of such DNA sequences can be prepared either as indicated namely by the PCR reaction, or by site directed mutagenesis [see e.g., Smith, Ann. Rev. Genet. 19, 423 (1985)] or synthetically as decribed, e.g., in EP 747 483 or by the usual methods of *Molecular Cloning* as described, e.g., in Sambrook et al. (s.a.).

As a host strain for the expression and/or amplification of the DNA sequences of the present invention, any microorganism may be used, e.g., those identified in EP 635 572, but it is preferable to use the strains belonging to the genus *Kurthia,* especially *Kurthia* sp. 538-6 (DSM No. 9454) and *Kurthia* sp. 538-51F9 (DSM No. 10610).

In order to obtain a transformant with a high biotin productivity, the DNA sequences of the present invention are used under the control of a promoter which is effective in such host cells. The DNA sequences of the present invention can be introduced into the host cell by transformation with a plasmid carrying such DNA sequences or by integration into the chromosome of the host cell.

When *Kurthia* sp. 538-51F9 is used as the host cell, *Kurthia* sp. 538-51F9 may be transformed with a hybrid plasmid carrying at least one gene involved in biotin biosynthesis isolated above from a *Kurthia* sp. strain. As a vector plasmid for the hybrid plasmid, pUB110 [J. Bacteriol., 154, 1184–1194, (1983)], pHP13 (Mol. Gen. Genet., 209, 335–342, 1987), or other plasmids comprising the origin of replication functioning in *Kurthia* sp. strain can be used. As DNA sequences for amplification and/or expression in *Kurthia* sp. any DNA sequence of the present invention can be used, but the DNA sequence corresponding to the bioB gene coding for biotin synthase is prefered. One example of such a hybrid plasmid is pYK114 shown in FIG. 14. In this plasmid the bioB gene is under the control of the promoter for the bioH gene and carries the replicating origin of pUB110.

*Kurthia* sp. 538-51F9 may be transformed with pYK114 obtained as described above by the protoplast transformation method [Molecular Biological Methods for Bacillus, 150, (1990)]. However, since *Kurthia* sp. 538-51F9 has a low efficiency of regeneration from protoplasts, transformation efficiency of this strain is very low. Therefore, it is preferred to use a strain having high efficiency of regeneration from protoplasts should be used, e.g., *Kurthia* sp. 538-51F9-RG21 which ca be prepared as described in Example 14 of the present case.

The present invention also provides a process for the production of biotin by the cultivation of the thus obtained transformants, and separation and purification of the produced biotin.

Cultivation of the biotin-expressing cells of the present invention can be done by methods known in the art. The culturing conditions are not critical so long as they are sufficient for the expression of biotin by the biotin-expresing cells to occur. A culture medium containing an assimilable carbon source, a digestible nitrogen source, an inorganic salt, and other nutrients necessary for the growth of the biotin-expressing cell can be used. As the carbon source, for example, glucose, fructose, lactose, galactose, sucrose, maltose, starch, dextrin or glycerol may be employed. As the nitrogen source, for example, peptone, soybean powder, corn steep liquor, meat extract, ammonium sulfate, ammonium nitrate, urea or a mixture thereof may be employed. Further, as an inorganic salt, sulfates, hydrochlorides or phosphates of calcium, magnesium, zinc, manganese, cobalt and iron can be employed. And, if necessary, conventional nutrient factors or an antifoaming agent, such as animal oil, vegetable oil or mineral oil can also be added. If the obtained biotin-expressing cell has an antibiotic resistant marker, the respective antibiotic should be supplemented into the medium. The pH of the culture medium may be between 5 to 9, preferably 6 to 8. The cultivation temperature can be 10 to 45° C., preferably 25 to 30° C. The cultivation time can be 1 to 10 days, preferably 2 to 7

The biotin produced under the conditions as described above can easily be isolated from the culture medium by methods known in the art. Thus, for example, after solid materials have been removed from the culture medium by filtration, the biotin in the filtrate may be absorbed on active carbon, then eluted and purified further with an ion exchange resin. Alternatively, the filtrate may be applied directly to an ion exchange resin and, after the elution, the biotin is recrystallized from a mixture of alcohol and water.

EXAMPLES

Example 1

Cloning bioB and bioF Genes of *Kurthia* sp. 538-KA26.

1. Preparation of the Genomic Library.

The acidomycin-resistant strain of *Kurthia* sp., 538-KA26 (DSM No. 10609), was cultivated in 100 ml of nutrient broth (Kyokuto Seiyaku Co; Honcho 3-1-1, Nihonbashi, Chuoh-Ku, Tokyo, Japan) at 30° C. overnight, and bacterial cells were recovered by centrifugation. The whole DNA was extracted from the bacterial cells by the phenol extraction method [Experiments with gene fusions, Cold Spring Harbor Laboratory, 137–138, (1984)], and 1.9 mg of the whole DNA was obtained.

The whole DNA (10 μg) was partially digested with 1.2 units of Sau3AI at 37° C. for 1 hour to yield fragments with around 10 Kb in length. 5–15 Kb DNA fragments were obtained by agarose gel electrophoresis.

The vector pBR322 (Takara Shuzo Co.) was completely digested with BamHI, and then treated with alkaline phosphatase to avoid self ligation. The DNA fragments were ligated with the cleaved pBR322 using a DNA ligation Kit (Takara Shuzo Co.) according to the instruction of the manufacturer. The ligation mixture was transferred to *Escherichia coli* JM109 (Takara Shuzo Co.) by the competent cell method [*Molecular Cloning*, Cold Spring Harbor Laboratory, 252–253, (1982)], and the strains were selected for ampicillin resistance (100 μg/ml) on agar plate LB medium (1% Bacto-tryptone, 0.5% Bacto-yeast extract, 0.5% NaCl, pH 7.5). About 5,000 individual clones having the genomic DNA fragments were obtained as a genomic library.

The ampicillin-resistant strains of the genomic library of *Kurthia* sp. 538-KA26 were cultivated at 37° C. overnight in 50 ml of LB medium containing 100 μg/ml ampicillin, and bacterial cells were collected by centrifugation. Plasmid DNA was extracted from the bacterial cells by the alkaline-denaturation method [*Molecular Cloning*, Cold Spring Harbor Laboratory, 90–91, (1982)].

2. Selection of the Clone Carrying the bioB Gene from the Genomic Library.

The plasmid DNA was transferred by the competent cell method into *Escherichia coli* bioB deficient mutant R875 (J. Bacteriol. 112, 830–839, 1972) without a biotin synthetase activity. The transformed *Escherichia coli* R875 cells were washed twice with 0.85% NaCl and streaked on 1.5% agar plates of M9CT medium (0.6% $Na_2HPO_4$, 0.3% $HK_2PO_4$, 0.05% NaCl, 0.1% $NH_4Cl$, 2 mM $MgSO_4$, 0.1 mM $CaCl_2$, 0.2% glucose, 0.6% vitamin-free casamino acid, 1 μg/ml thiamin) containing 100 μg/ml of ampicillin, and the plates were incubated at 37° C. for 40 hours. One transformant with the phenotype of the biotin prototrophy was obtained. The transformant was cultivated in LB medium containing 100 μg/ml ampicillin, and the hybrid plasmid was extracted from the cells. The hybrid plasmid carries an insert of 5.58 Kb and was designated pKB100. The restriction map is shown in FIGS. 1 and 2.

3. Complementation of Biotin Deficient Mutants of *Escherichia coli* with pKB100.

pKB100 was transferred to biotin deficient mutants of *Escherichia coli*, R875 (bioB⁻), W602 (bioA⁻), R878 (bioC⁻), R877 (bioD⁻), R874 (bioF⁻) or BM7086 (bioH⁻) [J. Bacteriol., 112, 830–839, (1972) and J. Bacteriol., 143, 789–800, (1980)], by the competent cell method. The transformed mutants were washed with 0.85% NaCl three times and plated on M9CT agar plates containing 100 μg/ml of ampicillin and 0.1 ng/ml biotin, and the plates were incubated at 37° C. overnight. Colonies on the plates were replicated on M9CT agar plates with 100 μg/ml ampicillin in the presence or absence of 0.1 ng/ml biotin, the plates were incubated at 37° C. for 24 hours to perform the complementation analysis. As shown in Table 1, the pKB100 could complement not only the bioB but also the bioF mutant. In contrast, bioA, bioC, bioD and bioH mutants were not complemented by pKB100. From this results, it was confirmed that the pKB100 carried the bioB and bioF genes of *Kurthia* sp. 538-KA26.

TABLE 1

| Plasmid | *Escherichia coli* biotin deficient mutant | | | | | |
|---|---|---|---|---|---|---|
| | bioA⁻ | bioB⁻ | bioC⁻ | bioD⁻ | bioF⁻ | bioH⁻ |
| pKB100 | − | + | − | − | + | − |
| pKB200 | − | + | − | + | − | − |
| pKB300 | + | | | | | |
| pKH100 | − | − | − | − | − | + |
| pKC100 | − | − | + | − | + | + |

Example 2

Isolation of Hybrid Plasmid Carrying of the bioD Gene of *Kurthia* sp. 538-KA26.

1. Isolation of the Hybrid Plasmid Carrying the bioD Gene.

The genomic library of *Kurthia* sp. 538-KA26 of Example 1-1 Was transferred into the *Escherichia coli* bioD deficient mutant R877, and transformants having an ampicillin resistance and biotin prototrophy phenotype were selected in the same manner as described in Example 1-2.

The transformant were cultivated at 37° C. overnight in LB medium with 100 μg/ml ampicillin, and the bacterial cells were collected by centrifugation. The hybrid plasmid was extracted from the cells by the alkaline-denaturation method. The hybrid plasmid had a 7.87 Kb insert DNA fragment and was designated pKB200. Cleavage patterns of pKB200 were analyzed using various restriction endonucleases (HindIII, NcoI, EcoRI, BglII, SalI, and PstI) and compared with that of pKB100. Restriction endonuclease analysis revealed that the two hybrid plasmids had exactly the same cleavage sites and that the 1.5 Kb DNA fragment was extended to the left side of pKB100 and the 0.8 Kb fragment was stretched out to the right side in the pKB200 (FIGS. 1 and 3).

2. Complementation of Biotin Deficient Mutant of *Escherichia coli* with pKB200.

The pKB200 was transferred to the biotin deficient mutants of *Escherichia coli*, R875 (bioB⁻), W602 (bioA⁻), R878 (bioC⁻), R877 (bioD⁻), R874 (bioF⁻) or BM 7086 (bioH⁻). Complementation analysis was performed by the method described in Example 1–3. The pKB200 complemented the bioD and bioB mutants, but not the bioA, bioC, bioF and bioH mutants as shown in Table 1. Although the pKB200 overlapped on the whole length of pKB100, pKB200 did not complement the bioF mutant.

Example 3

Isolation of the Hybrid Plasmid Carrying the bioH Gene of *Kurthia* sp. 538-KA26.

1. Isolation of the Hybrid Plasmid Carrying the bioH Gene.

Figure 4:
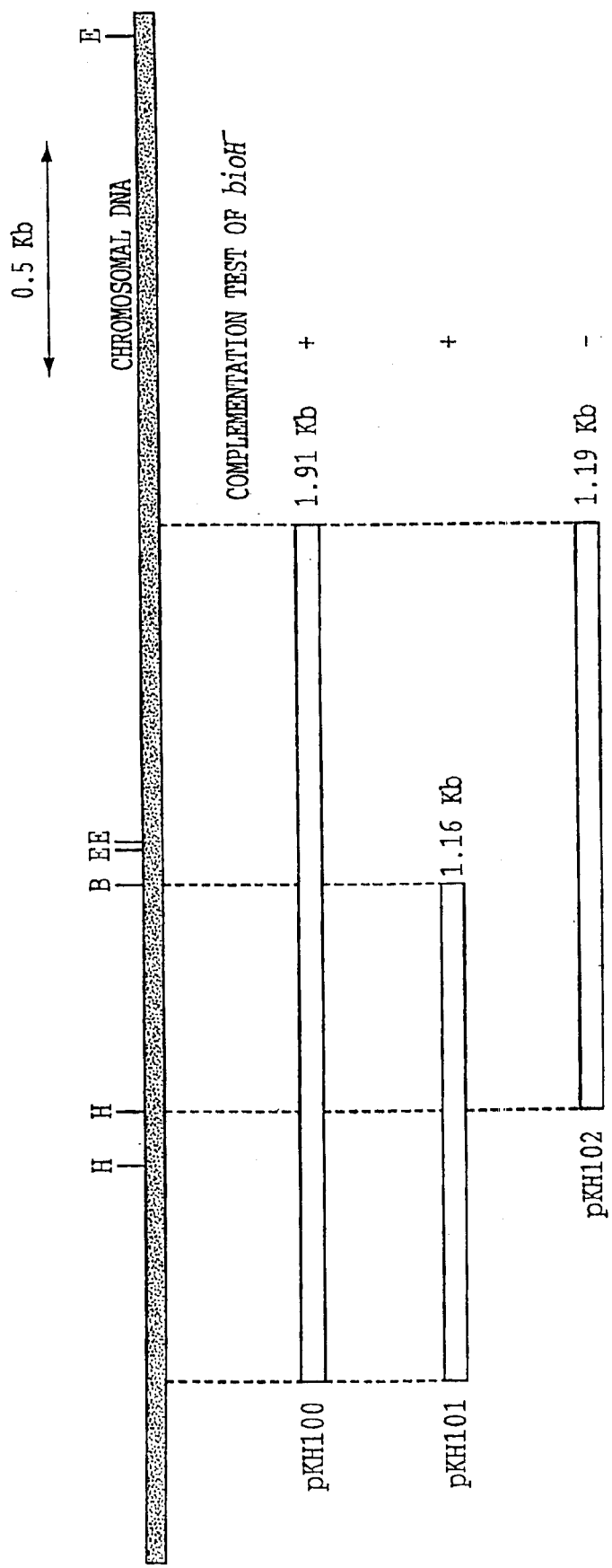
FIG. 4: Restriction maps and complementation results of pKH100, pKH101 and pKH102.
Figure 5:
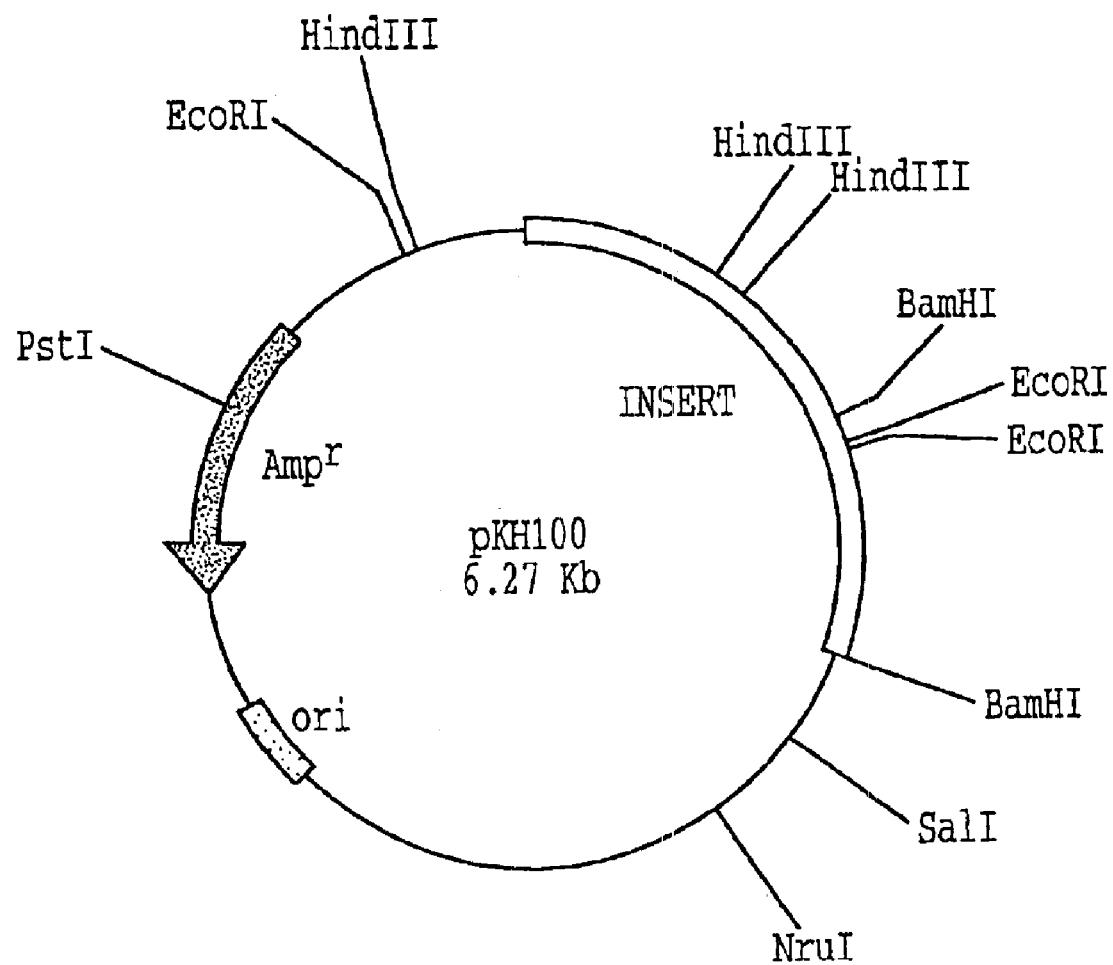
FIG. 5: Structure of pKH100.

The genomic library of *Kurthia* sp. 538-KA26 of Example 1–1 was transferred to the *Escherichia coli* bioH deficient mutant BM7086. Transformants having the bioH clone were selected for biotin prototrophy in the same manner as in Example 1–2. The hybrid plasmid were extracted from the transformed cells by the alkaline-denaturation method and analyzed by restriction enzymes. The hybrid plasmid had 1.91 Kb inserted DNA fragment and was designated pKH100. Since the genomic library used above has 5-15 Kb of the genomic DNA fragments, the pKH100 was thought to be subjected to a modification, such as deletion, in *Escherichia coli* strain. The restriction map of the pKH100 is shown in FIGS. 4 and 5. Cleavage patterns of the pKH100 were completely different from those of pKB100 and pKB200. Therefore, pKH100 carried a DNA fragment of the *Kurthia* chromosome which differed from those in pKB100 and pKB200.

2. Complementation of the Biotin Deficient Mutant of *Escherichia coli* with pKH100.

Complementation analysis was performed by the method described in Example 1-3. The pKH100 was transferred to the biotin deficient mutants of *Escherichia coli*, R875 (bioB⁻), W602 (bioA⁻), R878 (bioC⁻), R877 (bioD⁻), R874 (bioF⁻) or BM7086 (bioH⁻). pKH100 complemented only the bioH mutant, but not the bioB, bioA, bioC, bioD and bioF mutants as shown in Table 1. Thus, pKH100 carries the bioH gene.

Example 4

Isolation of the Hybrid Plasmid Carrying the bioC Gene of *Kurthia* sp. 538-KA26.

1. Isolation of the Hybrid Plasmid Carrying the bioC Gene.

The genomic library of *Kurthia* sp. 538-KA26 of Example 1-1 was transferred to the *Escherichia coli* bioC deficient mutant R878. Transformants with the bioC clone were selected for biotin prototrophy in the same manner as described in Example 1-2. The hybrid plasmid was extracted from the transformant cells by the alkaline-denaturation method and analyzed with restriction enzymes. The hybrid plasmid had a 6.76 Kb inserted DNA fragment and was designated pKC100. The restriction map of pKC100 is shown in FIGS. 6 and 7. Cleavage patterns of pKC100 were completely different from those of pKB100, pKB200 and pKH100. Therefore, pKC100 carries a different region of the *Kurthia* chromosome from those of pKB100, pKB200 and pKH100.

2. Complementation of the Biotin Deficient Mutant of *Escherichia coli* with pKC100.

The complementation analysis was performed by the method described in Example 1-3. pKC100 was transferred to the biotin deficient mutants of *Escherichia coli*, R875 (bioB⁻), W602 (bioA⁻), R878 (bioC⁻), R877 (bioD⁻), R874 (bioF⁻) or BM7086 (bioH⁻). pKC100 complemented the bioC, bioF and bioH mutants as shown in Table 1. Since the inserted DNA fragment in pKH100 was different from those in pKB100 and pKH100, pKC100 carried not only the bioC gene but also genes for isozymes of the bioF gene product (KAPA synthetase) and the bioH gene product.

Example 5

Isolation of the Hybrid Plasmid Carrying the bioA Gene of *Kurthia* sp. 538-KA26.

1. Isolation of the Left Region of the Chromosomal DNA in pKB200.

We isolated the left region of the chromosomal DNA in pKB200 from *Kurthia* sp. 538-KA26 chromosomal DNA by the hybridization method. The whole DNA of *Kurthia* sp. 538-KA26 was completely digested with HindIII and subjected to agarose gel electrophoresis. The DNA fragments on the gel were denatured and then transferred to a nylon membrane (Hybond-N, Amersham) according to the recommendations of the manufacturer.

pKB200 was completely digested with NcoI, and a 2.1 Kb NcoI fragment was isolated by agarose gel electrophoresis (FIG. 1). The NcoI fragment was labeled with $^{32}$P by the Multiprime DNA labeling system (Amersham) and used as a hybridization probe. The hybridization was performed on the membrane prepared above using the "Rapid hybridization buffer" (Amersham) according to the instructions of the manufacturer. The probe strongly hybridized to a HindIII fragment of about 8.5 Kb.

In order to isolate the 8.5 Kb fragment, the whole DNA of *Kurthia* sp. 538-KA26 was completely digested with HindIII, and 7.5–9.5 Kb DNA fragments were obtained by agarose gel electrophoresis. The vector plasmid pUC19 (Takara Shuzo Co.) was completely digested with HindIII and treated with alkaline phosphatase to avoid self ligation. The 7.5–9.5 Kb DNA fragments were ligated with the cleaved the pUC19 using a DNA ligation Kit (Takara Shuzo Co.), and the reaction mixture was transferred to *Escheri-*

*chia coli* JM109 by the competent cell method. About 1,000 individual clones carrying such genomic DNA fragments were obtained as a genomic library.

The selection was carried out by the colony hybridization method according to the protocol described by Maniatis et al. [*Molecular Cloning,* Cold Spring Harbor Laboratory, 312–328, (1982)]. The grown colonies on the agar plates were transferred to nylon membranes (Hybond-N, Amersham) and lysed by alkali. The denatured DNA was immobilized on the membranes. $^{32}P$ labeled NcoI fragments prepared as described above were used as a hybridization probe, and the hybridization was performed using the "Rapid hybridization buffer" (Amersham) according to the instructions of the manufacturer. Three colonies which hybridized with the probe DNA were obtained, and hybrid plasmids in these colonies were extracted by the alkaline-denaturation method.

The structure analysis was performed with restriction enzymes (BamHI, HindIII, NcoI, EcoRI, BglII, SalI and PstI). All of the three hybrid plasmids had a 8.44 Kb inserted DNA fragment, and the three hybrid plasmids had exactly the same cleavage patterns. These results indicated that they were identical. This hybrid plasmid was designated pKB300. The restriction map of pKB300 is shown in FIG. 1. About half length of the genomic DNA fragment in pKB300 overlappes with that of pKB200.

2. Complementation of the bioA Deficient Mutant of *Escherichia coli* with pKB300.

The complementation analysis of *Escherichia coli* W602 (bioA$^-$) with pKB300 was performed by the method described in Example 1-3. Since pKB300 complemented the bioA mutation (Table 1), pKB300 carries the bioA gene of *Kurthia* sp.

Example 6

Subcloning of the bioA, B, D and F Genes of *Kurthia* sp. 538-KA26.

Figure 8:
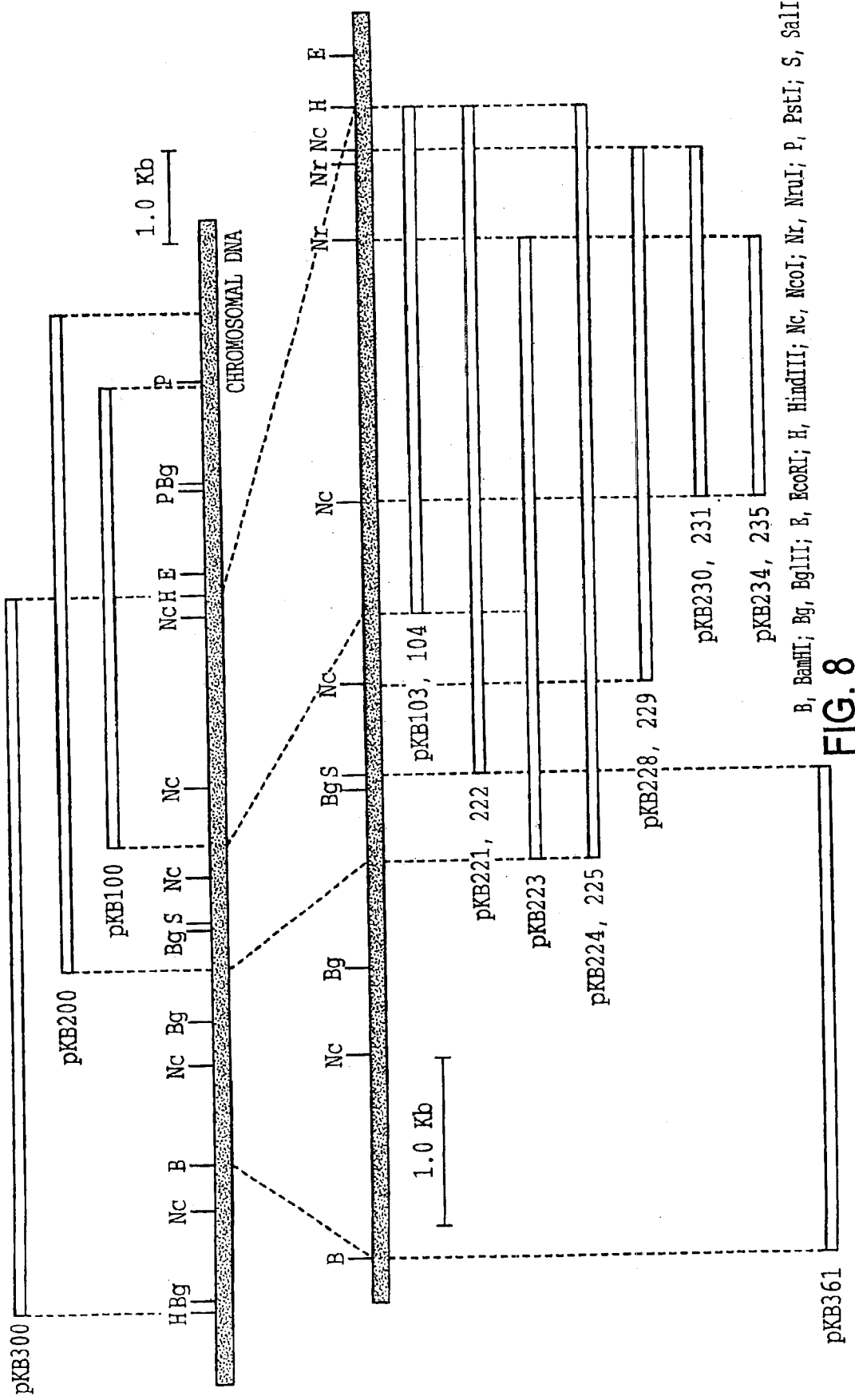
FIG. 8: Structures of derived plasmids from pKB100, pKB200 and pKB300.

1. Construction of the Hybrid Plasmid pKB103 and pKB104.

pKB100 was completely digested with HindIII, and a 3.3 Kb HindIII fragment was isolated. The 3.3 Kb fragment was ligated with the vector pUC18 (Takara Shuzo Co.) cleaved with HindIII using a DNA ligation Kit to construct the hybrid plasmids pKB103 and pKB104. In pKB103 and pKB104, the 3.3 Kb fragments were inserted in both orientations relative to the promoter-operator of the lac gene in pUC18. Their restriction map is shown in FIG. 8.

Complementation of the bioB or bioF deficient mutants of *Escherichia coli* (R875 or R874) were performed with pKB103 and pKB104 in the same manner as described in Example 1-3. pKB103 and pKB104 complemented the bioB and bioF mutants (Table 2).

2. Construction of Derivatives of pKB200.

Since pKB200 complemented the bioD mutation and covered the whole length of pKB100 carrying the bioB and bioF genes, a series of deletion mutations of pKB200 were constructed to localize more precisely bioB, bioD and bioF. A 4.0 Kb SalI-HindIII fragment of pKB200 was inserted into the SalI and HindIII sites of pUC18 and pUC19 to give pKB221 and pKB222 in which the SalI-HindIII fragment is placed in both orientations.

pKB200 was completely digested with NruI, and a 7.5 Kb NruI fragment was isolated by agarose gel electrophoresis. The NruI fragment was recirculated by the DNA ligation Kit, and pKB223 was obtained.

pKB200 was completely digested with HindIII. A 4.8 Kb HindIII fragment was isolated by agarose gel electrophoresis and cloned into the HindIII site of pUC18 in both orientations to generate pKB224 and pKB225.

pKB200 was partially digested with NcoI, and a 3.1 Kb NcoI fragment was isolated by agarose gel electrophoresis. The ends of the NcoI fragment were made blunt by using the Klenow fragment of the DNA polymerase I (Takara Shuzo Co.) and ligated with HindIII linker (Takara Shuzo Co.) The 3.1 Kb HindIII fragment was obtained by treatment with HindIII and cloned into the HindIII site of the pUC19 in both orientation to give pKB228 and pKB229.

In the same manner, both ends of a 2.1 Kb NcoI fragment of pKB200 were converted to HindIII sites by treatment with the Klenow fragment and addition of HindIII linkers. Then the obtained HindIII fragment was inserted into the HindIII site of pUC19 in both orientations to give pKB230 and pKB231.

pKB234 and pKB235 were generated by insertion of a 1.6 Kb HindIII-NruI fragment of pKB230 into the HindIII and SmaI sites of pUC19 and pUC18, respectively.

The restriction maps of the pKB200 derivatives are shown in FIG. 8.

3. Complementation Analysis of Biotin Deficient Mutants of *Escherichia coli* with pKB200 Derivatives.

Complementation analysis was performed with the pKB200 derivatives in the same manner as described in Example 1-3. The complementation results are summarized in Table 2. The bioB deficient mutant was complemented by pKB221, pKB222, pKB224 and pKB225, but not by pKB223, pKB228, pKB229, pKB230, pKB231, pKB234 and pKB235. The bioF deficient mutant was complemented by pKB223, pKB224, pKB225, pKB228 and pKB229, but not by pKB221, pKB222, pKB230, pKB231, pKB234 and pKB235. On the other hand, the bioD deficient mutant was complemented by pKB223, pKB224 and pKB225, but not by pKB221 and pKB222.

Together with the complementation analysis with pKB103 and pKB104, these results support that the bioF gene is present at the left side of the first NruI site on pKB103 while the bioB gene is located on the right side of the same NruI site with a short overlap to the left and that the bioD gene is present on at most 1.5 Kb left side region of the pKB200. Thus, the complementation results with various derivatives of pKB100 and pKB200 showed that the bioD, bioF and bioB genes lie in turn on the 4.4 Kb region at the left side of the HindIII site of pKB200.

4. Construction of the Hybrid Plasmid pKB361.

To determine the location of the bioA gene, the derivative of pKB300 was constructed. pKB361 was generated by insertion of a 2.8 Kb BamHI-SalI fragment of pKB300 into the BamHI and SalI sites of pUC19 (FIG. 8).

pKB361 was transferred to the bioA deficient mutant of *Escherichia coli* (W602), and complementation analysis was performed in the same manner as described in Example 1-3. The bioA mutant was complemented by pKB361 (Table 2), suggesting the presence of the bioA gene within the 2.8 Kb region between the BamHI and SalI sites of pKB300.

TABLE 2

Escherichia coli biotin deficient mutant

| Plasmid | bioA⁻ | bioD⁻ | bioF⁻ | bioB⁻ |
|---|---|---|---|---|
| pKB103, 104 | | | + | + |
| pKB221, 222 | | − | − | + |
| pKB223 | | + | + | − |
| pKB224, 225 | | + | + | + |
| pKB228, 229 | | | + | − |
| pKB230, 231 | | − | − | |
| pKB234, 235 | | − | − | |
| pKB361 | + | | | |

Example 7

Subcloning of the bioH Gene of *Kurthia* sp. 538-KA26

1. Construction of the Hybrid Plasmids pKH101 and pKH102.

pKH100 was completely digested with BamHI and recirculated with a DNA ligation Kit to generate pKH101 in which a 0.75 Kb BamHI fragment was deleted from pKH100 (FIG. 4). pKH102 was constructed from pKH100 by treatment with HindIII followed by recirculation with a DNA ligation Kit. The pKH102 lacked a 1.07 Kb HindIII fragment in pKH100 (FIG. 4).

Complementation analysis of the *Escherichia coli* bioH mutant (R878) was performed with pKH101 and pKH102 in the same manner as in Example 1-3. pKH101 complemented the bioH mutant, but not pKH102 (FIG. 4). This result indicated that the bioH gene is located in the left region (1.16 Kb) of the BamHI site on pKH100.

Example 8

Subcloning of the bioC Gene of *Kurthia* sp. 538-KA26 pKC100 was completely digested with BamHI, and a 1.81 Kb BamHI fragment was isolated by agarose gel electrophoresis. The BamHI fragment was ligated with pBR322 treated with BamHI and the Klenow fragment by a DNA ligation Kit. Finally, pKC101 and pKC102 in which the BamHI fragment was inserted in both orientations were obtained (FIG. 6).

pKC101 and pKC102 were transferred to the *Escherichia coli* bioC mutant R878, and complementation analysis was carried out in the same manner as in Example 1-3. The bioC mutant was complemented with pKC101 and pKC102, and the bioC gene was confirmed to lie in the 1.81 Kb BamHI fragment.

Example 9

Nucleotide Sequence of the Inserted DNA Fragments on pKB100, pKB200 and pKB300.

For nucleotide sequencing analysis of the inserted DNA fragments of pKB100, pKB200 and pKB300, several subclones overlapping mutually were constructed using pUC18, pUC19, M13mp18 and M13mp19 (Takara Shuzo Co.) and a series of deletion derivatives of the subclones were obtained by the Kilo-Sequencing Deletion Kit (Takara Shuzo Co.). Then, nucleotide sequencing analysis of the deletion derivatives was carried out by the dideoxy-chain termination technique (Sequenase version 2.0 DNA sequencing kit using 7-deaza-dGTP, United States Biochemical Co.). The results were analyzed by the computer program (GENETYX) from Software Development Co.

Computer analysis of this sequence revealed that the cloned DNA fragment has the capacity to code for six open reading frames (ORF). This gene operon has two gene clusters proceeding to both directions (FIG. 9-A).

The first ORF in the left gene cluster starts with the TTG codon preceded by a ribosomal binding site (RBS) with homology to the 3' end of the *Bacillus subtilis* 16S rRNA and codes for a protein of 194 amino acid residues having a molecular weight of 21,516. It was not possible to determine the function of the gene product by the complementation analysis, accordingly, this ORF was named ORF1.

The nucleotide sequence of the second ORF in the left gene cluster is shown in SEQ ID NO: 1. This gene codes for a protein of 236 amino acid residues with a molecular weight of 26,642. The predicted amino acid sequence of this gene product is shown in SEQ ID NO: 2. A putative RBS is found upstream of the ATG initiation codon. The complementation analysis (Example 6-3) showed that this ORF is the bioD gene.

The third ORF in the left gene cluster has a putative RBS upstream of the ATG initiation codon, and the nucleotide sequence of this gene is shown in SEQ ID NO: 3. This gene codes for a protein of 460 amino acid residues with a molecular weight of 51,731. The predicted amino acid sequence of this gene product is shown in SEQ ED NO: 4. This ORF was confirmed to correspond to the bioA gene (Example 6-3). An inverted repeat sequence was found to be located approximately 3 bp downstream from the termination codon. This structure may act as a transcriptional terminator.

The first ORF in the right gene cluster, named ORF2 starts at the ATG codon preceded by a putative RBS. This gene product is a protein consisting of 63 amino acid residues, and the calculated molecular weight is 7,447. We could not identify the function of this gene product by the complementation analysis and the amino acid sequence homology search. Accordingly, this ORF was named ORF2.

The nucleotide sequence of the second ORF in the right gene cluster is shown in SEQ ID NO: 5. This gene has three potential ATG initiation codons corresponding to the first, twenty-fifth and thirty-second amino acid residues. The complementation analysis (Example 6-3) showed that this ORF corresponds to the bioF gene. The predicted amino acid sequence of this gene product is shown in SEQ ID NO: 6. The molecular weight of the predicted protein with 387 amino acid residues was calculated to be 42,619, starting from the first initiation codon.

The third ORF in the right gene cluster as shown in SEQ ID NO: 7 has three potential initiation codons, two ATG codons (the first and eighteenth amino acid residues) and a GTG codon (the twelfth amino acid residue). The predicted amino acid sequence of this gene product is shown in SEQ ID NO: 8. The molecular weight of the predicted protein with 338 amino acid residues translated from the first initiation codon was calculated to be 37,438. The complementation analysis (Example 6-3) showed that this ORF corresponds to the bioB gene. The presence of an inverted repeat sequence 16 bp downstream from the termination codon is characteristic of a transcriptional terminator.

There were two possible promoter sequences forming face to face promoters between ORF1 and ORF2 as shown in FIG. 10. The transcriptions proceed to the left into the ORF1, bioD and bioA gene cluster, and to the right into the ORF2, bioF and bioB gene cluster. In addition, two transcriptional terminators were located downstream of the termination codons of the bioA and bioB genes. Therefore, the transcriptions in both directions generate two different mRNAs.

Two components of the inverted repeat sequences, Box1 and Box2, were found between the initiation site of the ORF1 and ORF2 genes (FIG. 10). The overall homology for the Box1 and Box2 is 82.5%. Comparison of the Box1 or Box2 with the operator of the *Escherichia coli* biotin operon [Nature, 276, 689–694, (1978)] showed that there is a high level of conservation (54.6% homology for both). The similarities between two inverted repeat sequences of the biotin operator of *Escherichia coli* suggest that the Box1 and Box2 must be involved in the negative control of the biotin synthesis by biotin.

Example 10

Nucleotide Sequence of the Inserted DNA Fragments of pKH100.

The nucleotide sequence analysis of the inserted DNA fragment of pKH100 was performed in the same manner as described in Example 9. A gene cluster containing two ORFs was found on the inserted DNA fragment (FIG. 9-B). In addition, it was confirmed that a part of the vector plasmid pBR322 and the inserted DNA fragment were deleted.

The first ORF as shown in SEQ D NO: 9 codes for a protein of 267 amino acid residues, and the calculated molecular weight is 29,423. The predicted amino acid sequence of this gene product is shown in SEQ ID NO: 10. A putative RBS is located at 6 bp upstream from the ATG initiation codon. The complementation analysis, as shown in Example 7, indicated that this ORF corresponds to the bioH gene.

The second ORF with a potential RBS was found downstream of the bioH gene. The ORF codes for a protein of 86 amino acid residues with a molecular weight of 9,955. The protein encoded by the ORF did not share homology with the biotin gene products of *Escherichia coli* and *Bacillus sphaericus*. The ORF was named ORF3.

A possible promoter sequence was found upstream from the initiation codon of the bioH gene as shown in FIG. 11. Since no inverted repeat sequence such as Box1 and Box2 was found in the 5'-noncoding region of the bioH gene, the transcription of this gene cluster must be not regulated. In addition, there is ah inverted repeat sequence overlapping with the termination codon of ORF3. Since this structure is able to act as a transcriptional terminator, the putative bioH promoter would therefore allow transcription of the bioH and ORF3 genes.

Example 11

Nucleotide Sequence of the Inserted DNA Fragments of pKC100.

The nucleotide sequence analysis of the inserted DNA fragment of pKC100 was performed in the same manner as described in Example 9. A gene cluster consisting of three ORFs was found on the inserted DNA fragment (FIG. 9-C).

The third ORF has a putative RBS upstream of the initiation codon and the nucleotide sequence of this gene is shown in SEQ ID NO: 15. This gene codes for a protein of 276 amino acid residues, and the calculated molecular weight is 31,599. The predicted amino acid sequence of this gene product is shown in SEQ ID NO: 16. The complementation analysis as shown in Example 8 indicating that this ORF corresponds to the bioC gene.

The first ORF as shown in SEQ ID NO: 11 codes for a protein of 398 amino acid residues with a molecular weight of 44,776. A putative RBS is located upstream of the initiation codon. The predicted amino acid sequence of this gene product as shown in SEQ ID NO: 12 has 43.0% homology with that of the bioF gene product of *Kurthia* sp. 538-KA26 in Example 9. Moreover, the pKC100 complemented the *Escherichia coli* bioF mutant as shown in Example 4. Therefore, this ORF was concluded to be a gene for an isozyme of the bioF gene product, KAPA synthetase. Therefore, this ORF was named bioFII gene.

The second ORF as shown in SEQ ID NO: 13 has a putative RBS upstream of the initiation codon. This gene codes for a protein of 248 amino acid residues with a molecular weight of 28,629. The predicted amino acid sequence of this gene product as shown in SEQ ID NO: 14 has 24.2% homology with that of the bioH gene product of *Kurthia* sp. 538-KA26 in Example 10. As shown in Example 4, the pKC100 also complemented the *Escherichia coli* bioH mutant. These results showed that this ORF is a gene for isozyme of the bioH gene product therefore this ORF was named bioHII gene.

A possible promoter sequence was found upstream from the initiation codon of the bioFII gene as shown in FIG. 12. An inverted sequence is located between the promoter sequence and the RBS of the bioFII gene. This inverted repeat sequence designated Box3 was compared with the Box1 and Box2 located between the ORF1 and ORF2 genes (Example 9). The Box1, Box2 and Box3 were extremely similar to each other (homology of Box1 and Box3 was 80.0% and that of Box2 and Box3 was 77.5%). Therefore, the cluster of the bioC gene must be regulated by a negative control similarly to the bioA cluster and the bioB cluster. In addition, there is an inverted repeat sequence 254 bp downstream of the termination codon of the bioC gene. This structure is thought to act as a transcriptional terminator.

Example 12

Figure 13:
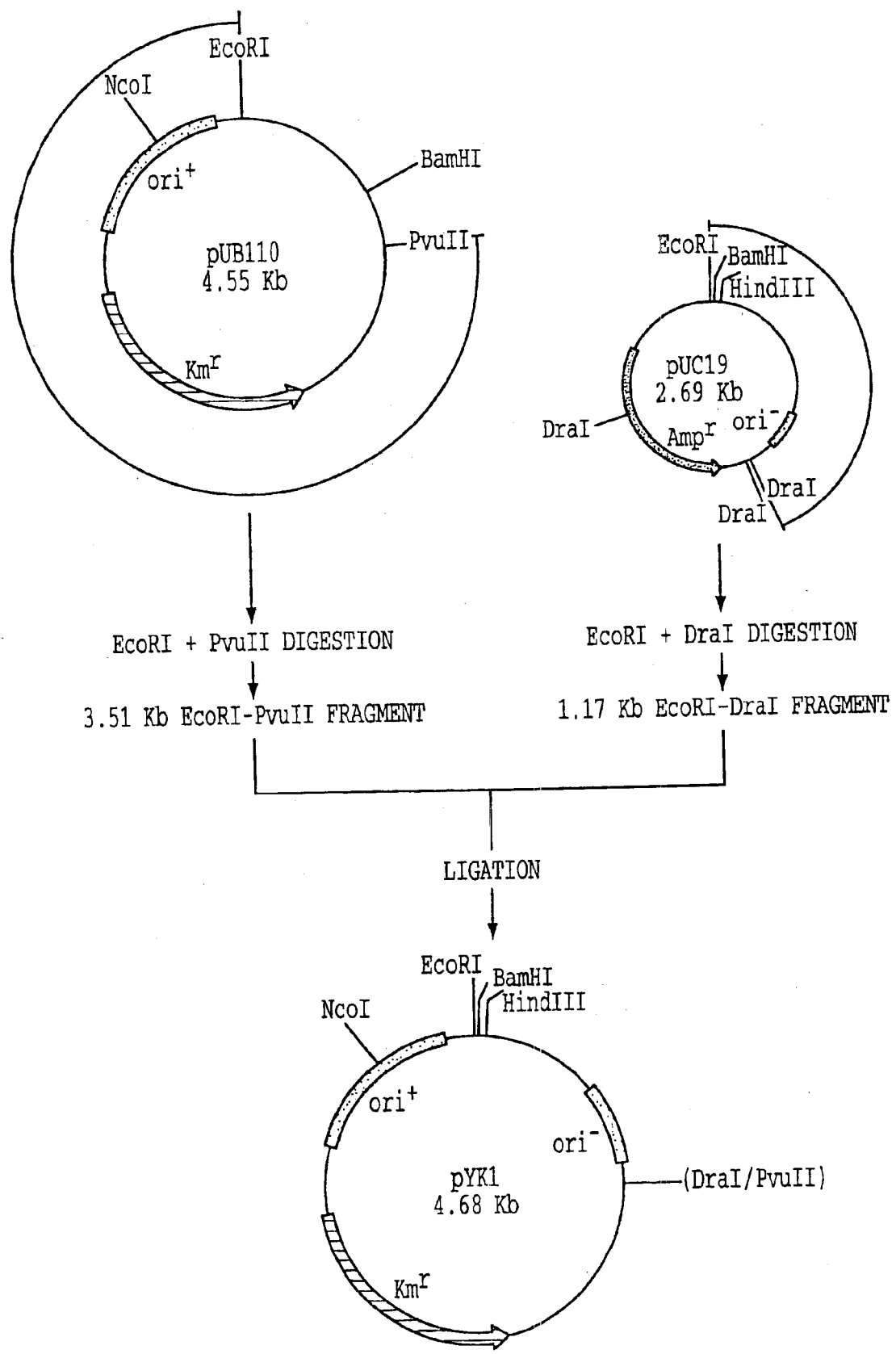
FIG. 13: Construction of the shuttle vector pYK1.

Construction of the Shuttle Vector for *Escherichia coli* and *Kurthia* sp. Strain A shuttle vector for *Escherichia coli* and *Kurthia* sp. was constructed by the strategy as shown in FIG. 13. The *Staphylococcus aureus* plasmid pUB110 (Bacillus Genetic Stock Center; The Ohio State University, Department of Biochemistry, 484 West Twelfth Avenue, Columbus, Ohio 43210, USA) was completely digested with EcoRI and PvuII. A 3.5 Kb EcoRI-PvuII fragment containing the replication origin for *Kurthia* sp. and the kanamycin resistant gene was isolated by agarose gel electrophoresis. The pUC19 was completely digested with EcoRI and DraI, and the 1.2 Kb EcoRI-DraI fragment having the replication origin of *Escherichia coli* was isolated by agarose gel electrophoresis. Then, these fragments were ligated with a DNA ligation Kit to generate the shuttle vector pYK1. pYK1 can replicate in *Escherichia coli* and *Kurthia* sp., and *Escherichia coli* or *Kurthia* sp. transformed by pYK1 show resistance to kanamycin.

Example 13

Figure 14:
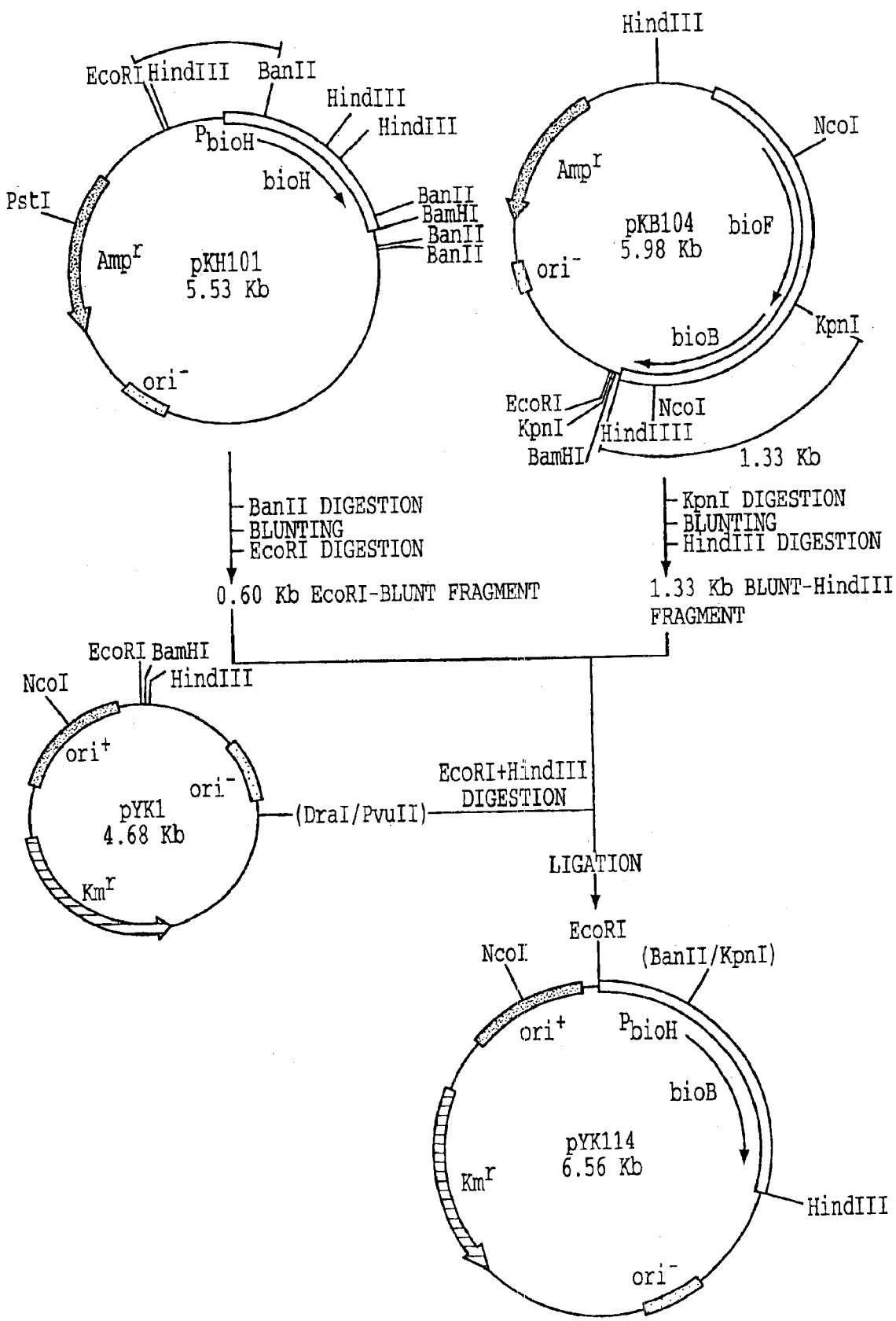
FIG. 14: Construction of the bioB expression plasmid pYK114.

Construction of the Expression Plasmid of the bioB Gene of *Kurthia* sp.

pYK114 in which the *Kurthia* bioB gene was inserted downstream of the promoter of the *Kurthia* bioH gene was constructed by the strategy as shown in FIG. 14. pKH101 of Example 7 was completely digested with BanII, and ends of BanII fragments were blunted by the Klenow fragment of the DNA polymerase. Then the BanII fragments were treated with EcoRI, and a 0.6 Kb EcoRI-blunt fragment containing the bioH promoter was isolated by agarose gel electrophoresis. pKB104 of Example 6 was completely digested with KpnI, and KpnI ends were changed to blunt ends by treatment with the Klenow fragment. After digestion with HindIII, a 1.3 Kb blunt-HindIII fragment carrying the bioB gene was isolated by agarose electrophoresis. The EcoRI-blunt and blunt-HindIII fragments were ligated with pYK1 digested with EcoRI and HindIII to construct pYK114. The bioB gene is constitutively expressed under the bioH promoter from pYK114.

Example 14

Isolation of the Derivative Strain of *Kurthia* sp. 538–51F9 with a High Transformation Efficiency

*Kurthia* sp. 538–51F9 (DSM No.10610) was cultivated at 28° C. in 50 ml of Tripticase Soy Broth (Becton Dickinson) until an optical density at 600 mn ($OD_{600}$) of 1.0. Grown cells were collected by centrifugation and suspended in SMM (0.5 M sucrose, 0.02M sodium maleate, 0.02 M $MgCl_2$ $6H_2O$; pH 6.5) at $OD_{600}$ 16. Then lysozyme (Sigma) was added to the cell suspension at 200 mg/ml, and the suspension was incubated at 30° C. for 90 minutes to form protoplasts. After the protoplasts have been washed with SMM twice, they were suspended in 0.5 ml of SMM. 1.5 ml of PEG solution (30% w/v polyethyleneglycol 4000 in SMM) was added to the protoplast suspension, and the suspension was incubated for 2 minutes on ice. Then 6 ml of SMM was added, and the protoplasts were collected by centrifugation. The collected protoplasts were suspended in SMM and incubated at 30° C. for 90 minutes. DM3 medium (0.5 M sodium succinate pH 7.3, 0.5% w/v casamino acid, 0.5% w/v yeast extract, 0.3% w/v $KH_2PO_4$, 0.7% w/v $K_2HPO_4$, 0.5% w/v glucose, 0.02 M $MgCl_2$ $6H_2O$, 0.01w/v bovine serum albumin) containing 0.6% agarose (Sigma; Type VII) was added to the protoplast suspension, and the suspension was overlaid on DM3 medium agar plates. The plates were incubated at 30° C. for 3 days. In total, 65 colonies regenerated on the DM3 plates were obtained.

The transformation efficiency of the regenerated strains was investigated with pYK1 of Example 12. As a result, 40 strains were selected and cultivated at 28° C. in 50 ml of Tripticase Soy Broth until $OD_{600}$ was 1.0. Grown cells were collected by centrifugation and suspended in SMM at $OD_{600}$ 16. Then the cells were treated with lysozyme by the method described above, and the protoplasts were obtained. The protoplasts were suspended in 0.5 ml SMM, and PYK1 (1 µg) was added to the protoplast suspensions. After addition of 1.5 ml of a PEG solution, the suspensions were incubated for 2 minutes on ice. 6 ml of SMM was added, and the protoplasts were collected by centrifugation. Then the protoplasts were suspended in SMM and incubated at 30° C. for 90 minutes. The DM3 medium containing 0.6% agarose was added to the protoplast suspensions, and the suspensions were overlaid on DM3 medium agar plates. The plates were incubated at 30° C. for 3 days. The DM3-agarose including the regenerated colonies on the plates were collected and spread on the nutrient broth agar plates with 5 µg/ml kanamycin to select the transformants. The plates were incubated overnight at 30° C. Finally, the derivative strain, *Kurthia* sp. 538–51F9-RG21, characterized by a high transformation efficiency (2,000 transformants per µg of DNA) was obtained.

Example 15

Amplification of the bioB Gene in *Kurthia* sp. 538–51F9-RG21

1. Transformation of *Kurthia* sp. 538–51F9-RG21.

The expression plasmid of the bioB gene of the *Kurthia* strain, pYK114, was constructed as described in Example 13. *Kurthia* sp. 538–51F9-RG21 was transformed with pYK114 and the vector plasmid pYK1 as described in Example 14. *Kurthia* sp. 538–51F9-RG21 carrying pYK1 or pYK114 was named *Kurthia* sp. 538–51F9-RG21 (pYK1) or *Kurt sp.* 538–51F9-RG21 (pYK114), respectively.

2. Biotin Production by Fermentation.

*Kurthia* sp. 538–51F9-RG21 (pYK1) and *Kurthia* sp 5351.F9-RG21-(pY-K114) were inoculated into 50 ml of the production medium (6% glycerol, 5.5% proteose peptone, 0.1% $KH_2PO_4$, 0.05% $MgSO_4$ $7H_2O$, 0.05% $FeSO_4$ $7H_2O$, 0.001% $MnSO_4$ $5H_2O$; pH 7.0) containing 5 µg/ml kanamycin. As a control, *Kurthia* sp. 538–51F9-RG21 was inoculated into 50 ml of the production medium. The cultivation was carried out at 28° C. for 120 hours.

After the cultivation, 2 ml of the culture broth was centrifuged to remove bacterial cells, and the supernatant was obtained. Biotin production in the supernatant was assayed by the microbiological assay using *Lactobacillus plantarum* (ATCC 8014). The amounts of produced biotin are given in Table 3.

TABLE 3

| Strain of Kurthia sp. | Biotin production (mg/L) |
|---|---|
| 51F9-RG21 | 15.4 |
| 51F9-RG21 (pYK1) | 14.3 |
| 51F9-RG21 (pYK114) | 39.0 |

What is claimed is:

1. An isolated DNA molecule comprising a polynucleotide selected from the group consisting of:
   a) SEQ ID NO: 7;
   b) a polynucleotide which encodes the polypeptide of SEQ ID NO: 8; and
   c) a polynucleotide which hybridizes to the complement of the polynucleotide from a) or b) under stringent hybridizing conditions, wherein the stringent conditions include hybridizing and washing in 0.2×SSC at about 65° C. and wherein the polynucleotide encodes a polypeptide having biotin synthase activity.

2. The isolated DNA molecule of claim 1 which comprises SEQ ID NO: 7.

3. An expression vector comprising a polynucleotide selected from the group consisting of:
   a) SEQ ID NO: 7;
   b) a polynucleotide which encodes the polypeptide of SEQ ID NO: 8; and
   c) a polynucleotide which hybridizes to the complement of the polynucleotide from a) or b) under stringent hybridizing conditions, wherein the stringent conditions include hybridizing and washing in 0.2×SSC at about 65° C. and wherein the polynucleotide encodes a polypeptide having biotin synthase activity.

4. The expression vector of claim 3 which comprises SEQ ID NO: 7.

5. A biotin-expressing cell transformed with an expression vector comprising polynucleotide selected from the group consisting of:
   a) SEQ ID NO: 7;
   b) a polynucleotide which encodes the polypeptide of SEQ ID NO: 8; and
   c) a polynucleotide which hybridizes to the complement of the polynucleotide from a) or b) under stringent hybridizing conditions, wherein the stringent conditions include hybridizing and washing in 0.2×SSC at about 65° C. and wherein the polynucleotide encodes a polypeptide having biotin synthase activity.

6. The cell of claim 5 in which the expression vector comprises SEQ ID NO: 7.

7. A process for the production of biotin comprising culturing a biotin-expressing cell transformed by an expression vector, wherein the expression vector comprises a polynucleotide selected from the group consisting of:
   a) SEQ ID NO: 7;
   b) a polynucleotide which encodes the polypeptide of SEQ ID NO: 8; and
   c) a polynucleotide which hybridizes to the complement of the polynucleotide from a) or b) under stringent hybridizing conditions, wherein the stringent conditions include hybridizing and washing in 0.2×SSC at about 65° C. and wherein the polynucleotide encodes a polypeptide having biotin synthase activity.

8. The process of claim 7 in which the expression vector comprises SEQ ID NO: 7.

* * * * *

SEQUENCE LISTING

<160> NUMBER OF SEQ ID NOS: 23

<210> SEQ ID NO 1
<211> LENGTH: 711
<212> TYPE: DNA
<213> ORGANISM: Kurthia sp.
<220> FEATURE:

```
<221> NAME/KEY: CDS
<222> LOCATION: (1)..(708)

<400> SEQUENCE: 1 atg ggt caa gcc tac ttt ata acc gga act ggc acg gat atc gga aaa      48
Met Gly Gln Ala Tyr Phe Ile Thr Gly Thr Gly Thr Asp Ile Gly Lys
1               5                   10                  15 acc gtc gcc acg agt tta ctc tat atg tct ctt caa aca atg gga aaa      96
Thr Val Ala Thr Ser Leu Leu Tyr Met Ser Leu Gln Thr Met Gly Lys
            20                  25                  30 agc gtc aca ata ttt aag ccg ttt caa aca gga ttg att cac gaa acg     144
Ser Val Thr Ile Phe Lys Pro Phe Gln Thr Gly Leu Ile His Glu Thr
        35                  40                  45 aat aca tac cct gac atc tct tgg ttt gag cag gaa ctt ggt gta aag     192
Asn Thr Tyr Pro Asp Ile Ser Trp Phe Glu Gln Glu Leu Gly Val Lys
    50                  55                  60 gca cct ggg ttt tac atg ctt gaa ccc gaa aca tct cca cac tta gct     240
Ala Pro Gly Phe Tyr Met Leu Glu Pro Glu Thr Ser Pro His Leu Ala
65                  70                  75                  80 ata aaa tta aca ggg caa caa atc gac gag caa aag gtc gtg gaa cga     288
Ile Lys Leu Thr Gly Gln Gln Ile Asp Glu Gln Lys Val Val Glu Arg
                85                  90                  95 gtt cac gaa ctc gaa caa atg tat gac atc gtg tta gtc gag ggc gct     336
Val His Glu Leu Glu Gln Met Tyr Asp Ile Val Leu Val Glu Gly Ala
            100                 105                 110 ggg gga ttg gcc gta cca ctc att gaa cga gcg aac agt ttc tat atg     384
Gly Gly Leu Ala Val Pro Leu Ile Glu Arg Ala Asn Ser Phe Tyr Met
        115                 120                 125 aca acc gat tta att aga gat tgc aac atg cca gtc att ttc gtt tct     432
Thr Thr Asp Leu Ile Arg Asp Cys Asn Met Pro Val Ile Phe Val Ser
    130                 135                 140 aca agc ggt tta gga tcg att cat aat gtc ata act acg cat tcg tat     480
Thr Ser Gly Leu Gly Ser Ile His Asn Val Ile Thr Thr His Ser Tyr
145                 150                 155                 160 gcc aaa ttg cat gat att agc gtt aaa act att tta tat aac cat tat     528
Ala Lys Leu His Asp Ile Ser Val Lys Thr Ile Leu Tyr Asn His Tyr
                165                 170                 175 cgg ccc gac gat gaa att cat cgt gac aat atc cta acc gtt gaa aag     576
Arg Pro Asp Asp Glu Ile His Arg Asp Asn Ile Leu Thr Val Glu Lys
            180                 185                 190 ctc aca gga ctc gct gac ctc gcc tgc ata cca aca ttt gtc gac gta     624
Leu Thr Gly Leu Ala Asp Leu Ala Cys Ile Pro Thr Phe Val Asp Val
        195                 200                 205 aga aaa gat ctg aga gtc tac ata ctt gat tta ctt agt aat cat gaa     672
Arg Lys Asp Leu Arg Val Tyr Ile Leu Asp Leu Leu Ser Asn His Glu
    210                 215                 220 ttt act caa caa cta aaa gag gtg ttc aag aat gaa tag                 711
Phe Thr Gln Gln Leu Lys Glu Val Phe Lys Asn Glu
225                 230                 235

<210> SEQ ID NO 2
<211> LENGTH: 236
<212> TYPE: PRT
<213> ORGANISM: Kurthia sp.

<400> SEQUENCE: 2

Met Gly Gln Ala Tyr Phe Ile Thr Gly Thr Gly Thr Asp Ile Gly Lys
1               5                   10                  15

Thr Val Ala Thr Ser Leu Leu Tyr Met Ser Leu Gln Thr Met Gly Lys
            20                  25                  30
```

```
Ser Val Thr Ile Phe Lys Pro Phe Gln Thr Gly Leu Ile His Glu Thr
        35                  40                  45

Asn Thr Tyr Pro Asp Ile Ser Trp Phe Glu Gln Glu Leu Gly Val Lys
 50                  55                  60

Ala Pro Gly Phe Tyr Met Leu Glu Pro Glu Thr Ser Pro His Leu Ala
 65                  70                  75                  80

Ile Lys Leu Thr Gly Gln Gln Ile Asp Glu Gln Lys Val Val Glu Arg
                 85                  90                  95

Val His Glu Leu Glu Gln Met Tyr Asp Ile Val Leu Val Glu Gly Ala
                100                 105                 110

Gly Gly Leu Ala Val Pro Leu Ile Glu Arg Ala Asn Ser Phe Tyr Met
            115                 120                 125

Thr Thr Asp Leu Ile Arg Asp Cys Asn Met Pro Val Ile Phe Val Ser
130                 135                 140

Thr Ser Gly Leu Gly Ser Ile His Asn Val Ile Thr Thr His Ser Tyr
145                 150                 155                 160

Ala Lys Leu His Asp Ile Ser Val Lys Thr Ile Leu Tyr Asn His Tyr
                165                 170                 175

Arg Pro Asp Glu Ile His Arg Asp Asn Ile Leu Thr Val Glu Lys
                180                 185                 190

Leu Thr Gly Leu Ala Asp Leu Ala Cys Ile Pro Thr Phe Val Asp Val
            195                 200                 205

Arg Lys Asp Leu Arg Val Tyr Ile Leu Asp Leu Leu Ser Asn His Glu
210                 215                 220

Phe Thr Gln Gln Leu Lys Glu Val Phe Lys Asn Glu
225                 230                 235
```

```
<210> SEQ ID NO 3
<211> LENGTH: 1383
<212> TYPE: DNA
<213> ORGANISM: Kurthia sp.
<220> FEATURE:
<221> NAME/KEY: CDS
<222> LOCATION: (1)..(1380)

<400> SEQUENCE: 3 atg aat agt cat gac tta gaa aag tgg gat aag gaa tat gta tgg cat    48
Met Asn Ser His Asp Leu Glu Lys Trp Asp Lys Glu Tyr Val Trp His
 1               5                  10                  15 ccg ttt aca caa atg aaa acg tat cga gaa agt aaa ccg cta atc att    96
Pro Phe Thr Gln Met Lys Thr Tyr Arg Glu Ser Lys Pro Leu Ile Ile
                 20                  25                  30 gaa cgc ggg gaa ggg agc tac ctt ttt gac ata gaa ggc aat cgg tac   144
Glu Arg Gly Glu Gly Ser Tyr Leu Phe Asp Ile Glu Gly Asn Arg Tyr
             35                  40                  45 ttg gac ggt tat gct tca tta tgg gtc aac gta cat ggc cat aat gaa   192
Leu Asp Gly Tyr Ala Ser Leu Trp Val Asn Val His Gly His Asn Glu
 50                  55                  60 cca gag cta aac aac gct ctc att gaa caa gtt gaa aaa gtc gca cac   240
Pro Glu Leu Asn Asn Ala Leu Ile Glu Gln Val Glu Lys Val Ala His
 65                  70                  75                  80 tca aca cta cta gga tct gca aat gta cca tcc ata tta ctg gct aag   288
Ser Thr Leu Leu Gly Ser Ala Asn Val Pro Ser Ile Leu Leu Ala Lys
                 85                  90                  95 aaa tta gca gag att act cct ggt cat tta tcg aaa gtc ttt tac tcg   336
Lys Leu Ala Glu Ile Thr Pro Gly His Leu Ser Lys Val Phe Tyr Ser
                100                 105                 110 gac act gga tca gct gct gta gaa atc tcc ctt aaa gtc gct tat caa   384
```

```
                Asp Thr Gly Ser Ala Ala Val Glu Ile Ser Leu Lys Val Ala Tyr Gln
                            115                 120                 125 tat tgg aaa aat atc gat cct gta aag tat caa cat aaa aat aaa ttt        432
Tyr Trp Lys Asn Ile Asp Pro Val Lys Tyr Gln His Lys Asn Lys Phe
        130                 135                 140 gtc tcc ctg aac gag gcg tac cac ggt gat aca gtt gga gca gtg agt        480
Val Ser Leu Asn Glu Ala Tyr His Gly Asp Thr Val Gly Ala Val Ser
145                 150                 155                 160 gtc ggc gga atg gat tta ttc cat aga atc ttt aaa cca cta cta ttt        528
Val Gly Gly Met Asp Leu Phe His Arg Ile Phe Lys Pro Leu Leu Phe
                165                 170                 175 gaa cgg att cca act cct tct cct tat aca tat cgc atg gct aaa cac        576
Glu Arg Ile Pro Thr Pro Ser Pro Tyr Thr Tyr Arg Met Ala Lys His
            180                 185                 190 ggg gat caa gaa gca gtg aaa aac tat tgt att gat gag ctg gaa aag        624
Gly Asp Gln Glu Ala Val Lys Asn Tyr Cys Ile Asp Glu Leu Glu Lys
        195                 200                 205 ttg ctt caa gac caa gca gag gaa att gca gga ttg att atc gaa ccg        672
Leu Leu Gln Asp Gln Ala Glu Glu Ile Ala Gly Leu Ile Ile Glu Pro
    210                 215                 220 ctt gtt caa gga gca gca ggc atc att acc cac cct cct ggc ttt tta        720
Leu Val Gln Gly Ala Ala Gly Ile Ile Thr His Pro Pro Gly Phe Leu
225                 230                 235                 240 aaa gcg gtc gaa caa ttg tgc aag aag tac aat ata tta ttg att tgt        768
Lys Ala Val Glu Gln Leu Cys Lys Lys Tyr Asn Ile Leu Leu Ile Cys
                245                 250                 255 gac gaa gta gcg gta gga ttt ggt cgc acc ggt aca tta ttt gcc tgt        816
Asp Glu Val Ala Val Gly Phe Gly Arg Thr Gly Thr Leu Phe Ala Cys
            260                 265                 270 gaa caa gaa gat gtc gtc cct gat att atg tgt atc ggt aaa gga att        864
Glu Gln Glu Asp Val Val Pro Asp Ile Met Cys Ile Gly Lys Gly Ile
        275                 280                 285 act ggc ggc tat atg cct ctg gcg gcc act atc atg aac gaa caa atc        912
Thr Gly Gly Tyr Met Pro Leu Ala Ala Thr Ile Met Asn Glu Gln Ile
    290                 295                 300 ttt aat tct ttt tta gga gag ccc gat gaa cat aaa acc ttc tat cac        960
Phe Asn Ser Phe Leu Gly Glu Pro Asp Glu His Lys Thr Phe Tyr His
305                 310                 315                 320 ggc cac acc tac aca ggg aat caa cta gcc tgt gcc ctg gcg ctg aag       1008
Gly His Thr Tyr Thr Gly Asn Gln Leu Ala Cys Ala Leu Ala Leu Lys
                325                 330                 335 aat atc gaa cta ata gaa aga cga gat ctc gtc aaa gac atc cag aag       1056
Asn Ile Glu Leu Ile Glu Arg Arg Asp Leu Val Lys Asp Ile Gln Lys
            340                 345                 350 aaa tcc aag cag cta tct gaa aaa ctg caa tcg cta tat gaa ctc ccg       1104
Lys Ser Lys Gln Leu Ser Glu Lys Leu Gln Ser Leu Tyr Glu Leu Pro
        355                 360                 365 att gtc ggt gat atc cgc cag cgc ggc ctc atg att gga ata gaa atc       1152
Ile Val Gly Asp Ile Arg Gln Arg Gly Leu Met Ile Gly Ile Glu Ile
    370                 375                 380 gtt aaa gat cgc caa aca aaa gaa ccg ttc aca atc caa gaa aat atc       1200
Val Lys Asp Arg Gln Thr Lys Glu Pro Phe Thr Ile Gln Glu Asn Ile
385                 390                 395                 400 gtt tca agc atc atc caa aac gct cgg gaa aat ggc ctg atc att cgg       1248
Val Ser Ser Ile Ile Gln Asn Ala Arg Glu Asn Gly Leu Ile Ile Arg
                405                 410                 415 gaa ctt ggc cct gtc atc aca atg atg ccc att ctt tcc atg tca gaa       1296
Glu Leu Gly Pro Val Ile Thr Met Met Pro Ile Leu Ser Met Ser Glu
            420                 425                 430
```

```
                                                                                          -continued aag gaa ctg aat act atg gtc gaa act gtc tac cgt tcg ata cag gac              1344
Lys Glu Leu Asn Thr Met Val Glu Thr Val Tyr Arg Ser Ile Gln Asp
            435                 440                 445 gtt tct gtg cac aac gga tta atc cca gca gca aac tga                          1383
Val Ser Val His Asn Gly Leu Ile Pro Ala Ala Asn
450                 455                 460

<210> SEQ ID NO 4
<211> LENGTH: 460
<212> TYPE: PRT
<213> ORGANISM: Kurthia sp.

<400> SEQUENCE: 4

Met Asn Ser His Asp Leu Glu Lys Trp Asp Lys Glu Tyr Val Trp His
 1               5                  10                  15

Pro Phe Thr Gln Met Lys Thr Tyr Arg Glu Ser Lys Pro Leu Ile Ile
                20                  25                  30

Glu Arg Gly Glu Gly Ser Tyr Leu Phe Asp Ile Glu Gly Asn Arg Tyr
            35                  40                  45

Leu Asp Gly Tyr Ala Ser Leu Trp Val Asn Val His Gly His Asn Glu
        50                  55                  60

Pro Glu Leu Asn Asn Ala Leu Ile Glu Gln Val Glu Lys Val Ala His
 65                  70                  75                  80

Ser Thr Leu Leu Gly Ser Ala Asn Val Pro Ser Ile Leu Leu Ala Lys
                85                  90                  95

Lys Leu Ala Glu Ile Thr Pro Gly His Leu Ser Lys Val Phe Tyr Ser
            100                 105                 110

Asp Thr Gly Ser Ala Ala Val Glu Ile Ser Leu Lys Val Ala Tyr Gln
        115                 120                 125

Tyr Trp Lys Asn Ile Asp Pro Val Lys Tyr Gln His Lys Asn Lys Phe
    130                 135                 140

Val Ser Leu Asn Glu Ala Tyr His Gly Asp Thr Val Gly Ala Val Ser
145                 150                 155                 160

Val Gly Gly Met Asp Leu Phe His Arg Ile Phe Lys Pro Leu Leu Phe
                165                 170                 175

Glu Arg Ile Pro Thr Pro Ser Pro Tyr Thr Tyr Arg Met Ala Lys His
            180                 185                 190

Gly Asp Gln Glu Ala Val Lys Asn Tyr Cys Ile Asp Glu Leu Glu Lys
        195                 200                 205

Leu Leu Gln Asp Gln Ala Glu Glu Ile Ala Gly Leu Ile Ile Glu Pro
    210                 215                 220

Leu Val Gln Gly Ala Ala Gly Ile Ile Thr His Pro Pro Gly Phe Leu
225                 230                 235                 240

Lys Ala Val Glu Gln Leu Cys Lys Lys Tyr Asn Ile Leu Leu Ile Cys
                245                 250                 255

Asp Glu Val Ala Val Gly Phe Gly Arg Thr Gly Thr Leu Phe Ala Cys
            260                 265                 270

Glu Gln Glu Asp Val Val Pro Asp Ile Met Cys Ile Gly Lys Gly Ile
        275                 280                 285

Thr Gly Gly Tyr Met Pro Leu Ala Ala Thr Ile Met Asn Glu Gln Ile
    290                 295                 300

Phe Asn Ser Phe Leu Gly Glu Pro Asp Glu His Lys Thr Phe Tyr His
305                 310                 315                 320

Gly His Thr Tyr Thr Gly Asn Gln Leu Ala Cys Ala Leu Ala Leu Lys
                325                 330                 335
```

```
Asn Ile Glu Leu Ile Glu Arg Arg Asp Leu Val Lys Asp Ile Gln Lys
            340                 345                 350

Lys Ser Lys Gln Leu Ser Glu Lys Leu Gln Ser Leu Tyr Glu Leu Pro
        355                 360                 365

Ile Val Gly Asp Ile Arg Gln Arg Gly Leu Met Ile Gly Ile Glu Ile
    370                 375                 380

Val Lys Asp Arg Gln Thr Lys Glu Pro Phe Thr Ile Gln Glu Asn Ile
385                 390                 395                 400

Val Ser Ser Ile Ile Gln Asn Ala Arg Glu Asn Gly Leu Ile Ile Arg
                405                 410                 415

Glu Leu Gly Pro Val Ile Thr Met Met Pro Ile Leu Ser Met Ser Glu
            420                 425                 430

Lys Glu Leu Asn Thr Met Val Glu Thr Val Tyr Arg Ser Ile Gln Asp
        435                 440                 445

Val Ser Val His Asn Gly Leu Ile Pro Ala Ala Asn
    450                 455                 460

<210> SEQ ID NO 5
<211> LENGTH: 1164
<212> TYPE: DNA
<213> ORGANISM: Kurthia sp.
<220> FEATURE:
<221> NAME/KEY: CDS
<222> LOCATION: (1)..(1161)

<400> SEQUENCE: 5 atg att tgg gag aag gaa cta gaa aag att aaa gaa gga ggg ctt tac      48
Met Ile Trp Glu Lys Glu Leu Glu Lys Ile Lys Glu Gly Gly Leu Tyr
 1               5                  10                  15 aga caa ctc caa acc gtt gaa aca atg agc gat caa ggg tat gcc atg      96
Arg Gln Leu Gln Thr Val Glu Thr Met Ser Asp Gln Gly Tyr Ala Met
            20                  25                  30 gtg aac gga aaa aaa atg atg atg ttt gcc tcc aat aat tac tta ggg     144
Val Asn Gly Lys Lys Met Met Met Phe Ala Ser Asn Asn Tyr Leu Gly
        35                  40                  45 att gcc aat gat caa cga tta att gag gct tct gtc caa gcg act caa     192
Ile Ala Asn Asp Gln Arg Leu Ile Glu Ala Ser Val Gln Ala Thr Gln
    50                  55                  60 aga ttt ggt acg ggt tct act ggt tca cga tta acc act ggc aat aca     240
Arg Phe Gly Thr Gly Ser Thr Gly Ser Arg Leu Thr Thr Gly Asn Thr
65                  70                  75                  80 att gtc cat gaa aaa cta gag aaa aga ctt gca gag ttt aag caa acg     288
Ile Val His Glu Lys Leu Glu Lys Arg Leu Ala Glu Phe Lys Gln Thr
                85                  90                  95 gat gca gcg ata gta tta aac aca ggg tat atg gct aac ata gca gcg     336
Asp Ala Ala Ile Val Leu Asn Thr Gly Tyr Met Ala Asn Ile Ala Ala
            100                 105                 110 tta acg acc ctt gtt ggt agt gac gat ctc att tta tcc gat gag atg     384
Leu Thr Thr Leu Val Gly Ser Asp Asp Leu Ile Leu Ser Asp Glu Met
        115                 120                 125 aat cat gcc agt att att gat ggc tgc cgt tta tca cgt gcg gaa act     432
Asn His Ala Ser Ile Ile Asp Gly Cys Arg Leu Ser Arg Ala Glu Thr
    130                 135                 140 atc att tat cgt cat gct gat tta ctt gac ttg gaa atg aaa ctc cag     480
Ile Ile Tyr Arg His Ala Asp Leu Leu Asp Leu Glu Met Lys Leu Gln
145                 150                 155                 160 att aat acc cgc tac agg aaa aga ata att gta acg gat ggc gtc ttt     528
Ile Asn Thr Arg Tyr Arg Lys Arg Ile Ile Val Thr Asp Gly Val Phe
                165                 170                 175
```

-continued

```
tcg atg gat ggt gat att gcg cca ttg cca ggt att gtc gaa ctt gcc    576
Ser Met Asp Gly Asp Ile Ala Pro Leu Pro Gly Ile Val Glu Leu Ala
        180                 185                 190 aag cgt tat gat gca ctt gtt atg gtg gat gac gca cat gcg acg ggt    624
Lys Arg Tyr Asp Ala Leu Val Met Val Asp Asp Ala His Ala Thr Gly
            195                 200                 205 gtt tta ggt aaa gac gga agg gga act tct gaa cat ttt gga ctg aag    672
Val Leu Gly Lys Asp Gly Arg Gly Thr Ser Glu His Phe Gly Leu Lys
    210                 215                 220 ggg aag ata gat atc gag atg ggg aca ctc tcc aaa gct gtt ggt gca    720
Gly Lys Ile Asp Ile Glu Met Gly Thr Leu Ser Lys Ala Val Gly Ala
225                 230                 235                 240 gaa gga ggg tat atc gct gga agc agg tct tta gtt gac tat gtc tta    768
Glu Gly Gly Tyr Ile Ala Gly Ser Arg Ser Leu Val Asp Tyr Val Leu
                245                 250                 255 aat cga gcc aga ccg ttt gtc ttc tct acc gcc tta tca gca gga gta    816
Asn Arg Ala Arg Pro Phe Val Phe Ser Thr Ala Leu Ser Ala Gly Val
            260                 265                 270 gta gca agt gca ctt aca gca gtc gat atc att caa tca gaa cct gaa    864
Val Ala Ser Ala Leu Thr Ala Val Asp Ile Ile Gln Ser Glu Pro Glu
    275                 280                 285 cgc aga gta cgc att cga gcc atg agc cag cgt ctt tat aat gaa tta    912
Arg Arg Val Arg Ile Arg Ala Met Ser Gln Arg Leu Tyr Asn Glu Leu
290                 295                 300 acc tcc ctt ggc tac aca gtt tcg ggg gga gaa act ccg att ctt gcc    960
Thr Ser Leu Gly Tyr Thr Val Ser Gly Gly Glu Thr Pro Ile Leu Ala
305                 310                 315                 320 att att tgc gga gaa ccg gaa cag gcc atg ttc ctt tcg aaa gaa tta    1008
Ile Ile Cys Gly Glu Pro Glu Gln Ala Met Phe Leu Ser Lys Glu Leu
                325                 330                 335 cat aag cac gga att tat gca cca gct atc cgt tcg cca acg gta cct    1056
His Lys His Gly Ile Tyr Ala Pro Ala Ile Arg Ser Pro Thr Val Pro
            340                 345                 350 ctt gga act tcg cgc att cga ctt acg tta atg gcg aca cat caa gaa    1104
Leu Gly Thr Ser Arg Ile Arg Leu Thr Leu Met Ala Thr His Gln Glu
    355                 360                 365 gaa caa atg aat cat gtt atc gac gtg ttc aga aca atc ctt acc aat    1152
Glu Gln Met Asn His Val Ile Asp Val Phe Arg Thr Ile Leu Thr Asn
370                 375                 380 aga tac aaa tag                                                    1164
Arg Tyr Lys
385
```

<210> SEQ ID NO 6
<211> LENGTH: 387
<212> TYPE: PRT
<213> ORGANISM: Kurthia sp.

<400> SEQUENCE: 6

```
Met Ile Trp Glu Lys Glu Leu Glu Lys Ile Lys Glu Gly Gly Leu Tyr
1               5                   10                  15

Arg Gln Leu Gln Thr Val Glu Thr Met Ser Asp Gln Gly Tyr Ala Met
            20                  25                  30

Val Asn Gly Lys Lys Met Met Phe Ala Ser Asn Asn Tyr Leu Gly
        35                  40                  45

Ile Ala Asn Asp Gln Arg Leu Ile Glu Ala Ser Val Gln Ala Thr Gln
    50                  55                  60

Arg Phe Gly Thr Gly Ser Thr Gly Ser Arg Leu Thr Thr Gly Asn Thr
65                  70                  75                  80
```

```
Ile Val His Glu Lys Leu Glu Lys Arg Leu Ala Glu Phe Lys Gln Thr
            85                  90                  95

Asp Ala Ala Ile Val Leu Asn Thr Gly Tyr Met Ala Asn Ile Ala Ala
            100                 105                 110

Leu Thr Thr Leu Val Gly Ser Asp Leu Ile Leu Ser Asp Glu Met
            115                 120                 125

Asn His Ala Ser Ile Ile Asp Gly Cys Arg Leu Ser Arg Ala Glu Thr
            130                 135                 140

Ile Ile Tyr Arg His Ala Asp Leu Leu Asp Leu Glu Met Lys Leu Gln
145                 150                 155                 160

Ile Asn Thr Arg Tyr Arg Lys Arg Ile Ile Val Thr Asp Gly Val Phe
            165                 170                 175

Ser Met Asp Gly Asp Ile Ala Pro Leu Pro Gly Ile Val Glu Leu Ala
            180                 185                 190

Lys Arg Tyr Asp Ala Leu Val Met Val Asp Asp Ala His Ala Thr Gly
            195                 200                 205

Val Leu Gly Lys Asp Gly Arg Gly Thr Ser Glu His Phe Gly Leu Lys
            210                 215                 220

Gly Lys Ile Asp Ile Glu Met Gly Thr Leu Ser Lys Ala Val Gly Ala
225                 230                 235                 240

Glu Gly Gly Tyr Ile Ala Gly Ser Arg Ser Leu Val Asp Tyr Val Leu
            245                 250                 255

Asn Arg Ala Arg Pro Phe Val Phe Ser Thr Ala Leu Ser Ala Gly Val
            260                 265                 270

Val Ala Ser Ala Leu Thr Ala Val Asp Ile Ile Gln Ser Glu Pro Glu
            275                 280                 285

Arg Arg Val Arg Ile Arg Ala Met Ser Gln Arg Leu Tyr Asn Glu Leu
            290                 295                 300

Thr Ser Leu Gly Tyr Thr Val Ser Gly Gly Glu Thr Pro Ile Leu Ala
305                 310                 315                 320

Ile Ile Cys Gly Glu Pro Gln Ala Met Phe Leu Ser Lys Glu Leu
            325                 330                 335

His Lys His Gly Ile Tyr Ala Pro Ala Ile Arg Ser Pro Thr Val Pro
            340                 345                 350

Leu Gly Thr Ser Arg Ile Arg Leu Thr Leu Met Ala Thr His Gln Glu
            355                 360                 365

Glu Gln Met Asn His Val Ile Asp Val Phe Arg Thr Ile Leu Thr Asn
            370                 375                 380

Arg Tyr Lys
385

<210> SEQ ID NO 7
<211> LENGTH: 1017
<212> TYPE: DNA
<213> ORGANISM: Kurthia sp.
<220> FEATURE:
<221> NAME/KEY: CDS
<222> LOCATION: (1)..(1014)

<400> SEQUENCE: 7 atg aga aaa gag gga tta ggt ttg gaa aca ttg gtg aaa aag gat tgg      48
Met Arg Lys Glu Gly Leu Gly Leu Glu Thr Leu Val Lys Lys Asp Trp
 1               5                  10                  15 aag atg cta gcg gaa aac gta atc aaa gga tat aaa gta aca gcg gaa      96
Lys Met Leu Ala Glu Asn Val Ile Lys Gly Tyr Lys Val Thr Ala Glu
                20                  25                  30
```

```
gaa gca ctt gct att gta caa gca cct gac aac gag gtt tta gag att      144
Glu Ala Leu Ala Ile Val Gln Ala Pro Asp Asn Glu Val Leu Glu Ile
         35                  40                  45 ttg aat gca gct ttc ctt att cgt cag cac tat tat gga aaa aag gtt      192
Leu Asn Ala Ala Phe Leu Ile Arg Gln His Tyr Tyr Gly Lys Lys Val
 50                  55                  60 aaa ttg aat atg atc att aat acg aag tca ggt cta tgt cct gaa gat      240
Lys Leu Asn Met Ile Ile Asn Thr Lys Ser Gly Leu Cys Pro Glu Asp
 65                  70                  75                  80 tgt ggc tat tgt tcg cag tca atc gtg tcg gaa gct cct atc gat aaa      288
Cys Gly Tyr Cys Ser Gln Ser Ile Val Ser Glu Ala Pro Ile Asp Lys
                 85                  90                  95 tat gct tgg ctg acc aaa gag aag att gtt gaa ggt gct caa gaa tca      336
Tyr Ala Trp Leu Thr Lys Glu Lys Ile Val Glu Gly Ala Gln Glu Ser
            100                 105                 110 att cgt cgc aaa gct ggc acg tat tgt atc gtt gct tct ggc cgt cgt      384
Ile Arg Arg Lys Ala Gly Thr Tyr Cys Ile Val Ala Ser Gly Arg Arg
        115                 120                 125 ccg acc aat agg gaa att gat cat gtc att gaa gct gtg aaa gaa att      432
Pro Thr Asn Arg Glu Ile Asp His Val Ile Glu Ala Val Lys Glu Ile
    130                 135                 140 cgc gag aca acg gat ctt aaa ata tgc tgc tgt cta ggt ttc tta aat      480
Arg Glu Thr Thr Asp Leu Lys Ile Cys Cys Cys Leu Gly Phe Leu Asn
145                 150                 155                 160 gaa acg cat gcc agt aag cta gct gaa gct ggg gtt cat cgc tac aag      528
Glu Thr His Ala Ser Lys Leu Ala Glu Ala Gly Val His Arg Tyr Lys
                165                 170                 175 cac aac tta aat aca tct caa gat aat tat aag aat att aca tcc aca      576
His Asn Leu Asn Thr Ser Gln Asp Asn Tyr Lys Asn Ile Thr Ser Thr
            180                 185                 190 cat act tat gag gac cgt gta gat aca gtc gaa gct gta aaa gag gcc      624
His Thr Tyr Glu Asp Arg Val Asp Thr Val Glu Ala Val Lys Glu Ala
        195                 200                 205 gga atg tct cca tgc tcg ggt gcc att ttt ggt atg aat gag tct aat      672
Gly Met Ser Pro Cys Ser Gly Ala Ile Phe Gly Met Asn Glu Ser Asn
    210                 215                 220 gaa gaa gca gta gag att gcc cta tcc cta cgc agt ctt gac gcg gat      720
Glu Glu Ala Val Glu Ile Ala Leu Ser Leu Arg Ser Leu Asp Ala Asp
225                 230                 235                 240 tct att cct tgt aat ttc ctc aat gcg att gac ggt aca cca ctt gag      768
Ser Ile Pro Cys Asn Phe Leu Asn Ala Ile Asp Gly Thr Pro Leu Glu
                245                 250                 255 gga act tcc gag ttg act cca act aaa tgt ttg aaa tta att tcg atg      816
Gly Thr Ser Glu Leu Thr Pro Thr Lys Cys Leu Lys Leu Ile Ser Met
            260                 265                 270 atg aga ttt gtt aat cca agt aag gaa atc cgt ctt gct gga ggt cgc      864
Met Arg Phe Val Asn Pro Ser Lys Glu Ile Arg Leu Ala Gly Gly Arg
        275                 280                 285 gag gtg aac ctc cgt tcc atg caa ccc atg gca ctt tat gca gcc aat      912
Glu Val Asn Leu Arg Ser Met Gln Pro Met Ala Leu Tyr Ala Ala Asn
    290                 295                 300 tct atc ttc gtc ggc gat tat cta aca aca gct gga caa gaa cct acg      960
Ser Ile Phe Val Gly Asp Tyr Leu Thr Thr Ala Gly Gln Glu Pro Thr
305                 310                 315                 320 gcg gat tgg ggc att atc gaa gac ctt ggt ttt gaa att gaa gaa tgc     1008
Ala Asp Trp Gly Ile Ile Glu Asp Leu Gly Phe Glu Ile Glu Glu Cys
                325                 330                 335 gct ctt taa                                                         1017
Ala Leu
```

<210> SEQ ID NO 8
<211> LENGTH: 338
<212> TYPE: PRT
<213> ORGANISM: Kurthia sp.

<400> SEQUENCE: 8

```
Met Arg Lys Glu Gly Leu Gly Leu Glu Thr Leu Val Lys Lys Asp Trp
 1               5                  10                  15

Lys Met Leu Ala Glu Asn Val Ile Lys Gly Tyr Lys Val Thr Ala Glu
             20                  25                  30

Glu Ala Leu Ala Ile Val Gln Ala Pro Asp Asn Glu Val Leu Glu Ile
         35                  40                  45

Leu Asn Ala Ala Phe Leu Ile Arg Gln His Tyr Tyr Gly Lys Lys Val
     50                  55                  60

Lys Leu Asn Met Ile Ile Asn Thr Lys Ser Gly Leu Cys Pro Glu Asp
 65                  70                  75                  80

Cys Gly Tyr Cys Ser Gln Ser Ile Val Ser Glu Ala Pro Ile Asp Lys
                 85                  90                  95

Tyr Ala Trp Leu Thr Lys Glu Lys Ile Val Glu Gly Ala Gln Glu Ser
            100                 105                 110

Ile Arg Arg Lys Ala Gly Thr Tyr Cys Ile Val Ala Ser Gly Arg Arg
        115                 120                 125

Pro Thr Asn Arg Glu Ile Asp His Val Ile Glu Ala Val Lys Glu Ile
    130                 135                 140

Arg Glu Thr Thr Asp Leu Lys Ile Cys Cys Cys Leu Gly Phe Leu Asn
145                 150                 155                 160

Glu Thr His Ala Ser Lys Leu Ala Glu Ala Gly Val His Arg Tyr Lys
                165                 170                 175

His Asn Leu Asn Thr Ser Gln Asp Asn Tyr Lys Asn Ile Thr Ser Thr
            180                 185                 190

His Thr Tyr Glu Asp Arg Val Asp Thr Val Glu Ala Val Lys Glu Ala
        195                 200                 205

Gly Met Ser Pro Cys Ser Gly Ala Ile Phe Gly Met Asn Glu Ser Asn
    210                 215                 220

Glu Glu Ala Val Glu Ile Ala Leu Ser Leu Arg Ser Leu Asp Ala Asp
225                 230                 235                 240

Ser Ile Pro Cys Asn Phe Leu Asn Ala Ile Asp Gly Thr Pro Leu Glu
                245                 250                 255

Gly Thr Ser Glu Leu Thr Pro Thr Lys Cys Leu Lys Leu Ile Ser Met
            260                 265                 270

Met Arg Phe Val Asn Pro Ser Lys Glu Ile Arg Leu Ala Gly Gly Arg
        275                 280                 285

Glu Val Asn Leu Arg Ser Met Gln Pro Met Ala Leu Tyr Ala Ala Asn
    290                 295                 300

Ser Ile Phe Val Gly Asp Tyr Leu Thr Thr Ala Gly Gln Glu Pro Thr
305                 310                 315                 320

Ala Asp Trp Gly Ile Ile Glu Asp Leu Gly Phe Glu Ile Glu Glu Cys
                325                 330                 335

Ala Leu
```

<210> SEQ ID NO 9
<211> LENGTH: 804
<212> TYPE: DNA
<213> ORGANISM: Kurthia sp.
<220> FEATURE:

-continued

```
<221> NAME/KEY: CDS
<222> LOCATION: (1)..(801)

<400> SEQUENCE: 9 atg cca ttc gta aat cat gac aat gaa agc ctt tac tat gag gtt cac        48
Met Pro Phe Val Asn His Asp Asn Glu Ser Leu Tyr Tyr Glu Val His
 1               5                  10                  15 gga caa ggt gat cct tta ttg ttg att atg ggg ctc ggc tat aac tct        96
Gly Gln Gly Asp Pro Leu Leu Leu Ile Met Gly Leu Gly Tyr Asn Ser
            20                  25                  30 tta tcc tgg cat aga acg gtg ccc act tta gct aag cgc ttt aaa gta       144
Leu Ser Trp His Arg Thr Val Pro Thr Leu Ala Lys Arg Phe Lys Val
        35                  40                  45 atc gtt ttt gat aat cgt ggt gtt ggt aag agc agt aag cct gaa cag       192
Ile Val Phe Asp Asn Arg Gly Val Gly Lys Ser Ser Lys Pro Glu Gln
 50                  55                  60 cca tat tct att gaa atg atg gct gag gat gca aga gcg gtc ctt gat       240
Pro Tyr Ser Ile Glu Met Met Ala Glu Asp Ala Arg Ala Val Leu Asp
 65                  70                  75                  80 gct gtt tcg gtt gac tca gca cat gta tat ggg att tca atg ggt gga       288
Ala Val Ser Val Asp Ser Ala His Val Tyr Gly Ile Ser Met Gly Gly
                85                  90                  95 atg att gcc caa agg ctg gca atc aca tat cca gaa cgt gtt cgt tct       336
Met Ile Ala Gln Arg Leu Ala Ile Thr Tyr Pro Glu Arg Val Arg Ser
            100                 105                 110 ctt gtt cta ggt tgt acc act gcg ggt ggt act act cat att caa cct       384
Leu Val Leu Gly Cys Thr Thr Ala Gly Gly Thr Thr His Ile Gln Pro
        115                 120                 125 tct cca gaa ata tct act tta atg gta tct cga gcc tcc ctt aca ggt       432
Ser Pro Glu Ile Ser Thr Leu Met Val Ser Arg Ala Ser Leu Thr Gly
    130                 135                 140 tct cca agg gat aat gcc tgg tta gcg gca cca ata gtt tat agt caa       480
Ser Pro Arg Asp Asn Ala Trp Leu Ala Ala Pro Ile Val Tyr Ser Gln
145                 150                 155                 160 gct ttt att gag aag cac cct gaa tta att cag gaa gat atc caa aag       528
Ala Phe Ile Glu Lys His Pro Glu Leu Ile Gln Glu Asp Ile Gln Lys
                165                 170                 175 cga ata gaa atc att act ccg cca agc gcc tat ctg tct caa cta caa       576
Arg Ile Glu Ile Ile Thr Pro Pro Ser Ala Tyr Leu Ser Gln Leu Gln
            180                 185                 190 gct tgt cta act cat gat aca tcc aat gaa ctt gat aaa ata aac ata       624
Ala Cys Leu Thr His Asp Thr Ser Asn Glu Leu Asp Lys Ile Asn Ile
        195                 200                 205 cca aca ttg att ata cac ggt gat gca gat aat ttg gtt cca tat gaa       672
Pro Thr Leu Ile Ile His Gly Asp Ala Asp Asn Leu Val Pro Tyr Glu
    210                 215                 220 aac ggt aaa atg tta gct gaa cgt att cag ggt tct cag ttt cac acc       720
Asn Gly Lys Met Leu Ala Glu Arg Ile Gln Gly Ser Gln Phe His Thr
225                 230                 235                 240 gta tcc tgt gct ggc cac att tat tta aca gaa gca gct aag gaa gca       768
Val Ser Cys Ala Gly His Ile Tyr Leu Thr Glu Ala Ala Lys Glu Ala
                245                 250                 255 aat gac aaa gtt ata cag ttt cta gct cat cta taa                       804
Asn Asp Lys Val Ile Gln Phe Leu Ala His Leu
            260                 265

<210> SEQ ID NO 10
<211> LENGTH: 267
<212> TYPE: PRT
<213> ORGANISM: Kurthia sp.
```

-continued

```
<400> SEQUENCE: 10

Met Pro Phe Val Asn His Asp Asn Glu Ser Leu Tyr Tyr Glu Val His
 1               5                  10                  15

Gly Gln Gly Asp Pro Leu Leu Ile Met Gly Leu Gly Tyr Asn Ser
             20                  25                  30

Leu Ser Trp His Arg Thr Val Pro Thr Leu Ala Lys Arg Phe Lys Val
         35                  40                  45

Ile Val Phe Asp Asn Arg Gly Val Gly Lys Ser Ser Lys Pro Glu Gln
     50                  55                  60

Pro Tyr Ser Ile Glu Met Met Ala Glu Asp Ala Arg Ala Val Leu Asp
 65                  70                  75                  80

Ala Val Ser Val Asp Ser Ala His Val Tyr Gly Ile Ser Met Gly Gly
             85                  90                  95

Met Ile Ala Gln Arg Leu Ala Ile Thr Tyr Pro Glu Arg Val Arg Ser
            100                 105                 110

Leu Val Leu Gly Cys Thr Thr Ala Gly Thr Thr His Ile Gln Pro
        115                 120                 125

Ser Pro Glu Ile Ser Thr Leu Met Val Ser Arg Ala Ser Leu Thr Gly
    130                 135                 140

Ser Pro Arg Asp Asn Ala Trp Leu Ala Ala Pro Ile Val Tyr Ser Gln
145                 150                 155                 160

Ala Phe Ile Glu Lys His Pro Glu Leu Ile Gln Glu Asp Ile Gln Lys
                165                 170                 175

Arg Ile Glu Ile Ile Thr Pro Pro Ser Ala Tyr Leu Ser Gln Leu Gln
            180                 185                 190

Ala Cys Leu Thr His Asp Thr Ser Asn Glu Leu Asp Lys Ile Asn Ile
        195                 200                 205

Pro Thr Leu Ile Ile His Gly Asp Ala Asp Asn Leu Val Pro Tyr Glu
    210                 215                 220

Asn Gly Lys Met Leu Ala Glu Arg Ile Gln Gly Ser Gln Phe His Thr
225                 230                 235                 240

Val Ser Cys Ala Gly His Ile Tyr Leu Thr Glu Ala Ala Lys Glu Ala
                245                 250                 255

Asn Asp Lys Val Ile Gln Phe Leu Ala His Leu
            260                 265

<210> SEQ ID NO 11
<211> LENGTH: 1197
<212> TYPE: DNA
<213> ORGANISM: Kurthia sp.
<220> FEATURE:
<221> NAME/KEY: CDS
<222> LOCATION: (1)..(1194)

<400> SEQUENCE: 11 atg cac agt gaa aaa caa tta cct tgt tgg gaa gaa aaa att aag aaa    48
Met His Ser Glu Lys Gln Leu Pro Cys Trp Glu Glu Lys Ile Lys Lys
 1               5                  10                  15 gaa ctg gct tat tta gaa gag ata tcg caa aaa cgt gaa ctc gtt tca    96
Glu Leu Ala Tyr Leu Glu Glu Ile Ser Gln Lys Arg Glu Leu Val Ser
             20                  25                  30 acg gaa ttc gcc gag cag cca tgg ctt atg atc aac ggg tgc aag atg   144
Thr Glu Phe Ala Glu Gln Pro Trp Leu Met Ile Asn Gly Cys Lys Met
         35                  40                  45 cta aat cta gct tct aat aac tat tta gga tat gca ggg gat gag cgg   192
Leu Asn Leu Ala Ser Asn Asn Tyr Leu Gly Tyr Ala Gly Asp Glu Arg
     50                  55                  60
```

```
ctg aaa aag gct atg gta gat gca gta cat aca tat ggt gca gga gcg       240
Leu Lys Lys Ala Met Val Asp Ala Val His Thr Tyr Gly Ala Gly Ala
 65                  70                  75                  80 acg gct tca cgt tta att att ggc aat cac cct ctt tac gag caa gca       288
Thr Ala Ser Arg Leu Ile Ile Gly Asn His Pro Leu Tyr Glu Gln Ala
                 85                  90                  95 gaa caa gct ctt gtc aat tgg aag aaa gcc gaa gca gga ctc att att       336
Glu Gln Ala Leu Val Asn Trp Lys Lys Ala Glu Ala Gly Leu Ile Ile
            100                 105                 110 aac agt gga tat aac gcg aac ctt gga att atc tcc acc ttg ctg tcc       384
Asn Ser Gly Tyr Asn Ala Asn Leu Gly Ile Ile Ser Thr Leu Leu Ser
        115                 120                 125 cgt aac gat att att tat agc gat aaa ttg aat cat gca agc att gtc       432
Arg Asn Asp Ile Ile Tyr Ser Asp Lys Leu Asn His Ala Ser Ile Val
    130                 135                 140 gat gga gct ctc tta agc cgt gca aag cat cta cgc tat cgt cat aat       480
Asp Gly Ala Leu Leu Ser Arg Ala Lys His Leu Arg Tyr Arg His Asn
145                 150                 155                 160 gat tta gat cat tta gaa gca tta ttg aaa aaa tca tcg atg gaa gca       528
Asp Leu Asp His Leu Glu Ala Leu Leu Lys Lys Ser Ser Met Glu Ala
                165                 170                 175 cgt aaa tta att gtg acg gat acg gtc ttc agc atg gac ggt gac ttt       576
Arg Lys Leu Ile Val Thr Asp Thr Val Phe Ser Met Asp Gly Asp Phe
            180                 185                 190 gct tat ctt gaa gac ctt gtt cgg tta aaa gaa cgt tat aac gct atg       624
Ala Tyr Leu Glu Asp Leu Val Arg Leu Lys Glu Arg Tyr Asn Ala Met
        195                 200                 205 tta atg aca gat gaa gca cac gga agc ggc atc tac ggt aaa aac ggt       672
Leu Met Thr Asp Glu Ala His Gly Ser Gly Ile Tyr Gly Lys Asn Gly
    210                 215                 220 gaa ggt tat gcc ggt cat ctc cat ctt caa aat aaa ata gat atc caa       720
Glu Gly Tyr Ala Gly His Leu His Leu Gln Asn Lys Ile Asp Ile Gln
225                 230                 235                 240 atg gga aca ttc agt aaa gcg ctc ggt tca ttc ggg gcc tat gtc gtc       768
Met Gly Thr Phe Ser Lys Ala Leu Gly Ser Phe Gly Ala Tyr Val Val
                245                 250                 255 ggg aaa aaa tgg ctc atc gac tat tta aaa aat cgc atg cgc gga ttc       816
Gly Lys Lys Trp Leu Ile Asp Tyr Leu Lys Asn Arg Met Arg Gly Phe
            260                 265                 270 ata tat tca act gca ctc ccc ccg gcc ata ctc ggt gct atg aaa aca       864
Ile Tyr Ser Thr Ala Leu Pro Pro Ala Ile Leu Gly Ala Met Lys Thr
        275                 280                 285 gcg ata gaa ctt gta cag caa gaa cca gaa cgc cgc tca ctg ctc caa       912
Ala Ile Glu Leu Val Gln Gln Glu Pro Glu Arg Arg Ser Leu Leu Gln
    290                 295                 300 aca cat tca gaa cac ttt aga gaa gaa ctc aca tat tac ggg ttt aat       960
Thr His Ser Glu His Phe Arg Glu Glu Leu Thr Tyr Tyr Gly Phe Asn
305                 310                 315                 320 att tgt gga agt cga tca caa att gtt cct atc gtc atc ggg gaa aac      1008
Ile Cys Gly Ser Arg Ser Gln Ile Val Pro Ile Val Ile Gly Glu Asn
                325                 330                 335 gaa aaa gcg atg gaa ttt gcc aca cgt ttg cag aaa gaa gga att gca      1056
Glu Lys Ala Met Glu Phe Ala Thr Arg Leu Gln Lys Glu Gly Ile Ala
            340                 345                 350 gct att gct gtc agg ccg ccg acc gtt cct gaa aat gag gcg aga atc      1104
Ala Ile Ala Val Arg Pro Pro Thr Val Pro Glu Asn Glu Ala Arg Ile
        355                 360                 365 cgt ttt act gta aca gct ctc cac gat aaa aaa gat ctt gat tgg gca      1152
Arg Phe Thr Val Thr Ala Leu His Asp Lys Lys Asp Leu Asp Trp Ala
```

```
              370                 375                 380
gtt gaa aaa gtt tcg atc att gga aaa gaa atg ggt gtt att taa            1197
Val Glu Lys Val Ser Ile Ile Gly Lys Glu Met Gly Val Ile
385                 390                 395
```

<210> SEQ ID NO 12
<211> LENGTH: 398
<212> TYPE: PRT
<213> ORGANISM: Kurthia sp.

<400> SEQUENCE: 12

```
Met His Ser Glu Lys Gln Leu Pro Cys Trp Glu Glu Lys Ile Lys Lys
 1               5                  10                  15

Glu Leu Ala Tyr Leu Glu Glu Ile Ser Gln Lys Arg Glu Leu Val Ser
            20                  25                  30

Thr Glu Phe Ala Glu Gln Pro Trp Leu Met Ile Asn Gly Cys Lys Met
        35                  40                  45

Leu Asn Leu Ala Ser Asn Asn Tyr Leu Gly Tyr Ala Gly Asp Glu Arg
 50                  55                  60

Leu Lys Lys Ala Met Val Asp Ala Val His Thr Tyr Gly Ala Gly Ala
 65                  70                  75                  80

Thr Ala Ser Arg Leu Ile Ile Gly Asn His Pro Leu Tyr Glu Gln Ala
                85                  90                  95

Glu Gln Ala Leu Val Asn Trp Lys Lys Ala Glu Ala Gly Leu Ile Ile
            100                 105                 110

Asn Ser Gly Tyr Asn Ala Asn Leu Gly Ile Ile Ser Thr Leu Leu Ser
        115                 120                 125

Arg Asn Asp Ile Ile Tyr Ser Asp Lys Leu Asn His Ala Ser Ile Val
130                 135                 140

Asp Gly Ala Leu Leu Ser Arg Ala Lys His Leu Arg Tyr Arg His Asn
145                 150                 155                 160

Asp Leu Asp His Leu Glu Ala Leu Leu Lys Lys Ser Ser Met Glu Ala
                165                 170                 175

Arg Lys Leu Ile Val Thr Asp Thr Val Phe Ser Met Asp Gly Asp Phe
            180                 185                 190

Ala Tyr Leu Glu Asp Leu Val Arg Leu Lys Glu Arg Tyr Asn Ala Met
        195                 200                 205

Leu Met Thr Asp Glu Ala His Gly Ser Gly Ile Tyr Gly Lys Asn Gly
210                 215                 220

Glu Gly Tyr Ala Gly His Leu His Leu Gln Asn Lys Ile Asp Ile Gln
225                 230                 235                 240

Met Gly Thr Phe Ser Lys Ala Leu Gly Ser Phe Gly Ala Tyr Val Val
                245                 250                 255

Gly Lys Lys Trp Leu Ile Asp Tyr Leu Lys Asn Arg Met Arg Gly Phe
            260                 265                 270

Ile Tyr Ser Thr Ala Leu Pro Pro Ala Ile Leu Gly Ala Met Lys Thr
        275                 280                 285

Ala Ile Glu Leu Val Gln Gln Glu Pro Glu Arg Arg Ser Leu Leu Gln
290                 295                 300

Thr His Ser Glu His Phe Arg Glu Glu Leu Thr Tyr Tyr Gly Phe Asn
305                 310                 315                 320

Ile Cys Gly Ser Arg Ser Gln Ile Val Pro Ile Val Ile Gly Glu Asn
                325                 330                 335

Glu Lys Ala Met Glu Phe Ala Thr Arg Leu Gln Lys Glu Gly Ile Ala
            340                 345                 350
```

<210> SEQ ID NO 13
<211> LENGTH: 747
<212> TYPE: DNA
<213> ORGANISM: Kurthia sp.
<220> FEATURE:
<221> NAME/KEY: CDS
<222> LOCATION: (1)..(744)

<400> SEQUENCE: 13

```
atg aaa cag ccg aat tta gtc atg ctt cct ggc tgg gga atg gaa aaa      48
Met Lys Gln Pro Asn Leu Val Met Leu Pro Gly Trp Gly Met Glu Lys
  1               5                  10                  15 gat gcg ttt caa ccg tta atc aaa ccg ctg tca gaa gta ttt cac ctc      96
Asp Ala Phe Gln Pro Leu Ile Lys Pro Leu Ser Glu Val Phe His Leu
             20                  25                  30 tca ttc ata gaa tgg aga gat atg aaa aca cta aat gac ttt gaa gaa     144
Ser Phe Ile Glu Trp Arg Asp Met Lys Thr Leu Asn Asp Phe Glu Glu
         35                  40                  45 cga gtc ata gac aca atc gct tct att gat ggt cct gtt ttt tta ctt     192
Arg Val Ile Asp Thr Ile Ala Ser Ile Asp Gly Pro Val Phe Leu Leu
     50                  55                  60 ggc tgg tca tta gga tct cta tta tca ctt gaa ctt gta agt tcg tat     240
Gly Trp Ser Leu Gly Ser Leu Leu Ser Leu Glu Leu Val Ser Ser Tyr
 65                  70                  75                  80 cga gaa aaa ata aaa ggt ttt ata cta att ggc gca aca agt cgt ttt     288
Arg Glu Lys Ile Lys Gly Phe Ile Leu Ile Gly Ala Thr Ser Arg Phe
                 85                  90                  95 acc aca gga gat aat tat tca ttt ggc tgg gat cca cga atg gtc gag     336
Thr Thr Gly Asp Asn Tyr Ser Phe Gly Trp Asp Pro Arg Met Val Glu
            100                 105                 110 cgc atg aag aaa caa ctg cag cgc aat aaa gag aag act ttg act tct     384
Arg Met Lys Lys Gln Leu Gln Arg Asn Lys Glu Lys Thr Leu Thr Ser
        115                 120                 125 ttc tat gaa gca atg ttt tcc gaa gct gaa aaa gaa gaa ggt ttt tat     432
Phe Tyr Glu Ala Met Phe Ser Glu Ala Glu Lys Glu Glu Gly Phe Tyr
    130                 135                 140 cat caa ttc atc acg aca att caa agc gag ttt cat ggg gat gac gta     480
His Gln Phe Ile Thr Thr Ile Gln Ser Glu Phe His Gly Asp Asp Val
145                 150                 155                 160 ttt tcg ctt ctt ata ggt ttg gat tat tta ctt cag aaa gat gtt aga     528
Phe Ser Leu Leu Ile Gly Leu Asp Tyr Leu Leu Gln Lys Asp Val Arg
                165                 170                 175 gta aag ctc gac cag att gaa act ccc att tta ttg atc cat ggg aga     576
Val Lys Leu Asp Gln Ile Glu Thr Pro Ile Leu Leu Ile His Gly Arg
            180                 185                 190 gaa gac aaa att tgt cca ctc gaa gcc tca tct ttc att aaa gaa aat     624
Glu Asp Lys Ile Cys Pro Leu Glu Ala Ser Ser Phe Ile Lys Glu Asn
        195                 200                 205 ctg ggt ggg aaa gcc gag gtt cat att atc gaa ggc gct ggt cat att     672
Leu Gly Gly Lys Ala Glu Val His Ile Ile Glu Gly Ala Gly His Ile
    210                 215                 220 cca ttt ttc aca aaa cca cag gaa tgt gtg cag ctt ata aaa aca ttt     720
Pro Phe Phe Thr Lys Pro Gln Glu Cys Val Gln Leu Ile Lys Thr Phe
```

```
att caa aag gag tac att cat gat tga                              747
Ile Gln Lys Glu Tyr Ile His Asp
            245
```

<210> SEQ ID NO 14
<211> LENGTH: 248
<212> TYPE: PRT
<213> ORGANISM: Kurthia sp.

<400> SEQUENCE: 14

```
Met Lys Gln Pro Asn Leu Val Met Leu Pro Gly Trp Gly Met Glu Lys
 1               5                  10                  15

Asp Ala Phe Gln Pro Leu Ile Lys Pro Leu Ser Glu Val Phe His Leu
            20                  25                  30

Ser Phe Ile Glu Trp Arg Asp Met Lys Thr Leu Asn Asp Phe Glu Glu
        35                  40                  45

Arg Val Ile Asp Thr Ile Ala Ser Ile Asp Gly Pro Val Phe Leu Leu
    50                  55                  60

Gly Trp Ser Leu Gly Ser Leu Leu Ser Leu Glu Leu Val Ser Ser Tyr
65                  70                  75                  80

Arg Glu Lys Ile Lys Gly Phe Ile Leu Ile Gly Ala Thr Ser Arg Phe
                85                  90                  95

Thr Thr Gly Asp Asn Tyr Ser Phe Gly Trp Asp Pro Arg Met Val Glu
            100                 105                 110

Arg Met Lys Lys Gln Leu Gln Arg Asn Lys Glu Lys Thr Leu Thr Ser
        115                 120                 125

Phe Tyr Glu Ala Met Phe Ser Glu Ala Glu Lys Glu Glu Gly Phe Tyr
    130                 135                 140

His Gln Phe Ile Thr Thr Ile Gln Ser Glu Phe His Gly Asp Asp Val
145                 150                 155                 160

Phe Ser Leu Leu Ile Gly Leu Asp Tyr Leu Leu Gln Lys Asp Val Arg
                165                 170                 175

Val Lys Leu Asp Gln Ile Glu Thr Pro Ile Leu Leu Ile His Gly Arg
            180                 185                 190

Glu Asp Lys Ile Cys Pro Leu Glu Ala Ser Ser Phe Ile Lys Glu Asn
        195                 200                 205

Leu Gly Gly Lys Ala Glu Val His Ile Ile Glu Gly Ala Gly His Ile
    210                 215                 220

Pro Phe Phe Thr Lys Pro Gln Glu Cys Val Gln Leu Ile Lys Thr Phe
225                 230                 235                 240

Ile Gln Lys Glu Tyr Ile His Asp
                245
```

<210> SEQ ID NO 15
<211> LENGTH: 831
<212> TYPE: DNA
<213> ORGANISM: Kurthia sp.
<220> FEATURE:
<221> NAME/KEY: CDS
<222> LOCATION: (1)..(828)

<400> SEQUENCE: 15

```
atg att gat aaa caa ttg tta agt aag cga ttc agt gaa cat gcg aaa    48
Met Ile Asp Lys Gln Leu Leu Ser Lys Arg Phe Ser Glu His Ala Lys
 1               5                  10                  15 aca tat gat gca tat gcc aat gtt caa aaa aac atg gcg aaa caa tta   96
Thr Tyr Asp Ala Tyr Ala Asn Val Gln Lys Asn Met Ala Lys Gln Leu
```

-continued

```
                  20                  25                  30
gtg gat ttg ctc cct caa aaa aac agc aaa caa aga att aac atc ctt      144
Val Asp Leu Leu Pro Gln Lys Asn Ser Lys Gln Arg Ile Asn Ile Leu
         35                  40                  45 gaa att ggc tgc ggt act ggt tac tta acc agg tta ctc gtt aat aca      192
Glu Ile Gly Cys Gly Thr Gly Tyr Leu Thr Arg Leu Leu Val Asn Thr
 50                  55                  60 ttt cct aat gct tct att acc gct gtt gat tta gca cca ggg atg gtt      240
Phe Pro Asn Ala Ser Ile Thr Ala Val Asp Leu Ala Pro Gly Met Val
 65                  70                  75                  80 gaa gtg gcg aaa gga ata aca atg gaa gac cgt gtt act ttt tta tgt      288
Glu Val Ala Lys Gly Ile Thr Met Glu Asp Arg Val Thr Phe Leu Cys
                 85                  90                  95 gct gat atc gaa gaa atg acg ctt aat gaa aat tac gac tta att att      336
Ala Asp Ile Glu Glu Met Thr Leu Asn Glu Asn Tyr Asp Leu Ile Ile
            100                 105                 110 tct aat gca acg ttt caa tgg ctg aat aat ctt cct gga acc att gaa      384
Ser Asn Ala Thr Phe Gln Trp Leu Asn Asn Leu Pro Gly Thr Ile Glu
        115                 120                 125 caa ttg ttt aca cga tta acg cct gaa gga aac ctg ata ttt tca acg      432
Gln Leu Phe Thr Arg Leu Thr Pro Glu Gly Asn Leu Ile Phe Ser Thr
    130                 135                 140 ttt gga att aaa acc ttt caa gag ctt cat atg tcc tat gaa cat gcg      480
Phe Gly Ile Lys Thr Phe Gln Glu Leu His Met Ser Tyr Glu His Ala
145                 150                 155                 160 aaa gaa aag ctt caa ctt tca att gat agt tca cca ggc caa ctg ttt      528
Lys Glu Lys Leu Gln Leu Ser Ile Asp Ser Ser Pro Gly Gln Leu Phe
                165                 170                 175 tac gct cta gaa gaa tta tcc caa att tgt gaa gaa gca atc cct ttt      576
Tyr Ala Leu Glu Glu Leu Ser Gln Ile Cys Glu Glu Ala Ile Pro Phe
            180                 185                 190 tca tca gca ttt cca tta gag ata aca aaa ata gaa aag ctt gaa cta      624
Ser Ser Ala Phe Pro Leu Glu Ile Thr Lys Ile Glu Lys Leu Glu Leu
        195                 200                 205 gag tac ttt cag aca gta cgt gaa ttt ttc act tca att aaa aag att      672
Glu Tyr Phe Gln Thr Val Arg Glu Phe Phe Thr Ser Ile Lys Lys Ile
    210                 215                 220 ggt gca gct aac agc aac aaa gaa aac tac tgc cag cgc cct tct ttt      720
Gly Ala Ala Asn Ser Asn Lys Glu Asn Tyr Cys Gln Arg Pro Ser Phe
225                 230                 235                 240 ttt cga gag tta atc aac ata tac gaa aca aaa tac caa gat gaa tca      768
Phe Arg Glu Leu Ile Asn Ile Tyr Glu Thr Lys Tyr Gln Asp Glu Ser
                245                 250                 255 ggt gtg aag gca acc tat cac tgt ttg ttt ttt aag ata ata aaa cat      816
Gly Val Lys Ala Thr Tyr His Cys Leu Phe Phe Lys Ile Ile Lys His
            260                 265                 270 gcc ccc cta ccc taa                                                   831
Ala Pro Leu Pro
        275
```

<210> SEQ ID NO 16
<211> LENGTH: 276
<212> TYPE: PRT
<213> ORGANISM: Kurthia sp.

<400> SEQUENCE: 16

```
Met Ile Asp Lys Gln Leu Leu Ser Lys Arg Phe Ser Glu His Ala Lys
  1               5                  10                  15

Thr Tyr Asp Ala Tyr Ala Asn Val Gln Lys Asn Met Ala Lys Gln Leu
             20                  25                  30
```

```
Val Asp Leu Leu Pro Gln Lys Asn Ser Lys Gln Arg Ile Asn Ile Leu
        35                  40                  45

Glu Ile Gly Cys Gly Thr Gly Tyr Leu Thr Arg Leu Leu Val Asn Thr
    50                  55                  60

Phe Pro Asn Ala Ser Ile Thr Ala Val Asp Leu Ala Pro Gly Met Val
65                  70                  75                  80

Glu Val Ala Lys Gly Ile Thr Met Glu Asp Arg Val Thr Phe Leu Cys
                85                  90                  95

Ala Asp Ile Glu Glu Met Thr Leu Asn Glu Asn Tyr Asp Leu Ile Ile
                100                 105                 110

Ser Asn Ala Thr Phe Gln Trp Leu Asn Asn Leu Pro Gly Thr Ile Glu
            115                 120                 125

Gln Leu Phe Thr Arg Leu Thr Pro Glu Gly Asn Leu Ile Phe Ser Thr
        130                 135                 140

Phe Gly Ile Lys Thr Phe Gln Glu Leu His Met Ser Tyr Glu His Ala
145                 150                 155                 160

Lys Glu Lys Leu Gln Leu Ser Ile Asp Ser Ser Pro Gly Gln Leu Phe
                165                 170                 175

Tyr Ala Leu Glu Glu Leu Ser Gln Ile Cys Glu Ala Ile Pro Phe
                180                 185                 190

Ser Ser Ala Phe Pro Leu Glu Ile Thr Lys Ile Glu Lys Leu Glu Leu
            195                 200                 205

Glu Tyr Phe Gln Thr Val Arg Glu Phe Phe Thr Ser Ile Lys Lys Ile
        210                 215                 220

Gly Ala Ala Asn Ser Asn Lys Glu Asn Tyr Cys Gln Arg Pro Ser Phe
225                 230                 235                 240

Phe Arg Glu Leu Ile Asn Ile Tyr Glu Thr Lys Tyr Gln Asp Glu Ser
                245                 250                 255

Gly Val Lys Ala Thr Tyr His Cys Leu Phe Phe Lys Ile Ile Lys His
            260                 265                 270

Ala Pro Leu Pro
        275

<210> SEQ ID NO 17
<211> LENGTH: 360
<212> TYPE: DNA
<213> ORGANISM: Kurthia sp.
<220> FEATURE:
<221> NAME/KEY: RBS
<222> LOCATION: Complement((67)..(76))
<220> FEATURE:
<221> NAME/KEY: -35_signal
<222> LOCATION: (210)..(215)
<220> FEATURE:
<221> NAME/KEY: -10_signal
<222> LOCATION: (234)..(239)
<220> FEATURE:
<221> NAME/KEY: -10_signal
<222> LOCATION: Complement((235)..(240))
<220> FEATURE:
<221> NAME/KEY: RBS
<222> LOCATION: (289)..(293)
<220> FEATURE:
<221> NAME/KEY: misc_feature
<222> LOCATION: (302)..(358)
<223> OTHER INFORMATION: Partial sequence of ORF2.
<220> FEATURE:
<221> NAME/KEY: misc_feature
<222> LOCATION: (125)..(164)
<223> OTHER INFORMATION: BOX1 - inverted repeat
<220> FEATURE:
<221> NAME/KEY: misc_feature
```

```
<222> LOCATION: (244)..(283)
<223> OTHER INFORMATION: BOX2 - inverted repeat
<220> FEATURE:
<221> NAME/KEY: misc_feature
<222> LOCATION: Complement((1)..(58))
<223> OTHER INFORMATION: Partial sequnce of ORF1.

<400> SEQUENCE: 17
cgccaatggc agttaacgca gtaaataggg caacataaga gatcgtttta gctttcaagt     60
tttcaacctc cttttttaa aattggtagg taaaatgccc actattagtg tgcatgattt     120
atattttata tgtcaaccat ttattatttt agtaacata taaagcgcaa ttaaaatgac      180
agacttagaa aaatattgaa aattagtaat tgaacaatat tttatttgtg tgttattata    240
caatttatat gttaactatt ttaagatata gttaacatat aaaggcttgg agggaacaaa    300
tatgacagga gaaatgttaa tacaggatga actttccaga gaaacagcgg tatttgtggc    360

<210> SEQ ID NO 18
<211> LENGTH: 20
<212> TYPE: PRT
<213> ORGANISM: Kurthia sp.

<400> SEQUENCE: 18

Leu Lys Ala Lys Thr Ile Ser Tyr Val Ala Leu Phe Thr Ala Leu Thr
 1               5                  10                  15

Ala Ile Gly Ala
            20

<210> SEQ ID NO 19
<211> LENGTH: 20
<212> TYPE: PRT
<213> ORGANISM: Kurthia sp.

<400> SEQUENCE: 19

Met Thr Gly Glu Met Leu Ile Gln Asp Glu Leu Ser Arg Glu Thr Ala
 1               5                  10                  15

Val Phe Val Ala
            20

<210> SEQ ID NO 20
<211> LENGTH: 240
<212> TYPE: DNA
<213> ORGANISM: Kurthia sp.
<220> FEATURE:
<221> NAME/KEY: -35_signal
<222> LOCATION: (65)..(70)
<220> FEATURE:
<221> NAME/KEY: -10_signal
<222> LOCATION: (91)..(96)
<220> FEATURE:
<221> NAME/KEY: RBS
<222> LOCATION: (127)..(135)
<220> FEATURE:
<221> NAME/KEY: CDS
<222> LOCATION: (142)..(240)
<223> OTHER INFORMATION: bioH

<400> SEQUENCE: 20
actaacccct atggtgtcca gattaagcgt aatgtagtat aggattttag tcaattagca     60 attttttgaaa tatttagtac gatcacataa tagaatcata tataatgatt aaaatattaa    120
ttacagaaaa gaggtatttt c atg cca ttc gta aat cat gac aat gaa agc      171
                        Met Pro Phe Val Asn His Asp Asn Glu Ser
                         1               5                  10 ctt tac tat gag gtt cac gga caa ggt gat cct tta ttg ttg att atg     219
Leu Tyr Tyr Glu Val His Gly Gln Gly Asp Pro Leu Leu Leu Ile Met
```

```
Leu Tyr Tyr Glu Val His Gly Gln Gly Asp Pro Leu Leu Leu Ile Met
            15                  20                  25 ggg ctc ggc tat aac tct tta                                           240
Gly Leu Gly Tyr Asn Ser Leu
            30
```

<210> SEQ ID NO 21
<211> LENGTH: 33
<212> TYPE: PRT
<213> ORGANISM: Kurthia sp.

<400> SEQUENCE: 21

```
Met Pro Phe Val Asn His Asp Asn Glu Ser Leu Tyr Tyr Glu Val His
 1               5                   10                  15

Gly Gln Gly Asp Pro Leu Leu Leu Ile Met Gly Leu Gly Tyr Asn Ser
            20                  25                  30

Leu
```

<210> SEQ ID NO 22
<211> LENGTH: 300
<212> TYPE: DNA
<213> ORGANISM: Kurthia sp.
<220> FEATURE:
<221> NAME/KEY: -35_signal
<222> LOCATION: (83)..(88)
<220> FEATURE:
<221> NAME/KEY: -10_signal
<222> LOCATION: (107)..(112)
<220> FEATURE:
<221> NAME/KEY: misc_feature
<222> LOCATION: (115)..(154)
<223> OTHER INFORMATION: Box 3 - inverted repeat
<220> FEATURE:
<221> NAME/KEY: RBS
<222> LOCATION: (154)..(161)
<220> FEATURE:
<221> NAME/KEY: misc_feature
<222> LOCATION: (168)..(299)
<223> OTHER INFORMATION: Partial sequence of bioFII (full gene is SEQ ID
      NO: 11).

<400> SEQUENCE: 22

```
ttatgataag tgtcttttt cgccccttga tttctcctag attaatggat aatcaattta      60
ttatcatgtt cctttcaaa gcttgacagt tcattgagt catgattaga atgttttata     120
tgttaaccta tattatttt agttaacata taaaaggag aatggctatg cacagtgaaa     180
aacaattacc ttgttgggaa gaaaaaatta agaaagaact ggcttattta gaagagatat   240
cgcaaaaacg tgaactcgtt tcaacggaat tcgccgagca gccatggctt atgatcaacg   300
```

<210> SEQ ID NO 23
<211> LENGTH: 45
<212> TYPE: PRT
<213> ORGANISM: Kurthia sp.

<400> SEQUENCE: 23

```
Met His Ser Glu Lys Gln Leu Pro Cys Trp Glu Glu Lys Ile Lys Lys
 1               5                   10                  15

Glu Leu Ala Tyr Leu Glu Glu Ile Ser Gln Lys Arg Glu Leu Val Ser
            20                  25                  30

Thr Glu Phe Ala Glu Gln Pro Trp Leu Met Ile Asn Gly
            35                  40                  45
```